(12) United States Patent
Weidmann et al.

(10) Patent No.: US 9,969,858 B2
(45) Date of Patent: May 15, 2018

(54) METALLOINSERTOR CONJUGATES

(71) Applicant: CALIFORNIA INSTITUTE OF TECHNOLOGY, Pasadena, CA (US)

(72) Inventors: Alyson Weidmann, San Jose, CA (US); Jacqueline K. Barton, San Marino, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 81 days.

(21) Appl. No.: 15/011,476

(22) Filed: Jan. 29, 2016

(65) Prior Publication Data

US 2016/0222043 A1    Aug. 4, 2016

Related U.S. Application Data

(60) Provisional application No. 62/109,474, filed on Jan. 29, 2015, provisional application No. 62/111,563, filed on Feb. 3, 2015.

(51) Int. Cl.
  *C08K 3/08* (2006.01)
  *A61K 31/28* (2006.01)
  *A61K 31/555* (2006.01)

(52) U.S. Cl.
  CPC .............. *C08K 3/08* (2013.01); *A61K 31/28* (2013.01); *A61K 31/555* (2013.01)

(58) Field of Classification Search
  CPC ...................................................... C08K 3/08
  USPC ....................................................... 514/188
  See application file for complete search history.

(56) References Cited

U.S. PATENT DOCUMENTS

2013/0345189 A1* 12/2013 Barton ................. C07D 241/36
                                                         514/185

FOREIGN PATENT DOCUMENTS

WO    WO2012155004    * 11/2012

OTHER PUBLICATIONS

Ernst et al. (J. Am. Chem. Soc. (2009), vol. 131, pp. 2359-2366).*
Komor et al. (J. Am. Chem. Soc. (2012, vol. 134, pp. 19223-19333).*
Basu, Amitabha et al. "Copper Complexes of 1,1-Di-2-pyridylethanol: X-Ray Structures and Reaction with Oxygen"; J. Chem. Soc.; Chem Commun.; 1987; 22; pp. 1724-1725.
Brabec, Viktor et al.; "DNA interstrand cross-links of trans-diamminedichloroplatinum(II) are preferentially formed between guanine and complementary cytosine residues"; Proc. Natl. Acad. Sci. USA; Jun. 1993; vol. 90; pp. 5345-5349.
Gandolfi, Ottavio et al.; "Aminomalonato(1,2-diaminocyclohexane)platinum(II): A Competitive Antitumor Compound Within a New Class of Neutral, Chemically Stable, Water Soluble, Functionalized Platinum(II) Complexes"; Inorganica Chimica Acta; 1987; 135; pp. 27-31.
Graztner, Howard G.; "Monoclonal antibody to 5-Bromo- and 5-Iododeoxyuridine: A New Reagent for Detection of DNA Replication"; Science; Oct. 29, 1982; vol. 218; pp. 474-475.
Greenwald, Richard B. et al.; "Effective drug delivery by PEGylated drug conjugates"; Adv. Drug Del. Rev.; 2003; vol. 55; Issue 2; pp. 217-250.
Greenwald, R.B.; "PEG drugs: an overview"; J. Controlled Release; 2001; vol. 74; pp. 159-171.
Kirin, Srecko I. et al.; "Synthesis and Characterization of Cu Complexes with Amino Acid Substituted Di(2-pyridyl)amine Ligands"; Eur. J. Inorg. Chem.; 2007; pp. 3686-3694.
Komor, Alexis C. et al.; "Cell-selective biological activity of rhodium metalloinsertors correlates with subcellular localization"; J. Am. Chem. Soc.; Nov. 21, 2012; 134(46); pp. 19223-19233.
Molineux, Graham; "Pegylation: engineering improved biopharmaceuticals for oncology"; Pharmacotherapy; 2003; vol. 23; No. 8; pp. 3S-8S.
Mosmann, Tim; "Rapid colorimetric assay for cellular growth and survival: application to proliferation and cytotoxicity assays"; J. Immunol. Methods, 1983; vol. 65; pp. 55-63.
Mürner, Hansruedi et al.; "A Versatile Synthetic Approach to Rhodium(III) Diimine Metallointercalators: Condensation of o-Quinones with Coordinated cis-Ammines"; Inorg. Chem.; 1998; 37; pp. 3007-3012.
Roberts, M.J. et al.; "Chemistry for peptide and protein PEGylation"; Adv. Drug Deliv. Rev.; 2012; vol. 64; pp. 116-127.
Smith, P.K. et al.; "Measurement of protein using bicinchoninic acid"; Analytical Biochemistry; 1985; vol. 150; pp. 76-85.
Weidmann, Alyson G. et al.; "Biological effects of simple changes in functionality on rhodium metalloinsertors"; Philos. Trans. R. Soc. A.; Jun. 2013; vol. 371; Issue 1995; 13pp.

* cited by examiner

*Primary Examiner* — Kendra D Carter
*Assistant Examiner* — Taina D Matos Negron
(74) *Attorney, Agent, or Firm* — Lewis Roca Rothgerber Christie LLP

(57) ABSTRACT

A composition including a metalloinsertor conjugate that specifically targets mismatch repair (MMR)-deficient cells includes a complex represented by Formula I.

$M^{m+}(L_1)(L_2)(L_3)(L_4)(L_5)$    Formula I

Selective cytotoxicity may be induced in MMR-deficient cells upon uptake of the metalloinsertor conjugate. Metalloinsertor complexes conjugated with platinum (Pt) may allow for more specific targeting of platinum anticancer agents.

10 Claims, 29 Drawing Sheets
(3 of 29 Drawing Sheet(s) Filed in Color)

[Rh(chrysi)(phen)(HPBA)]$^{2+}$ rac-[Rh(chrysi)(phen)(L-cysteine)]$^{2+}$

[Rh(chrysi)(phen)(DPE-Pt(NH$_3$)$_2$Cl)]$^{3+}$

[Rh(chrysi)(HDPA)(Amal)Pt(DACH)]³⁺

FIG. 7
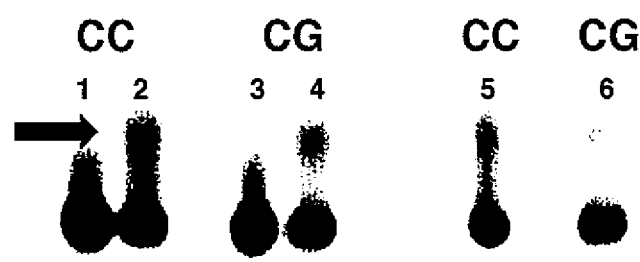
P³²* 5'-TTAGGATCAT<u>C</u>CATATA-3'
3'-AATCCTCGTA<u>C</u>GTATAT-5'
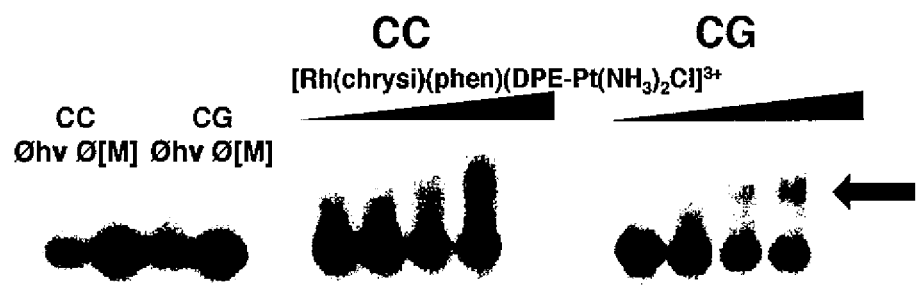

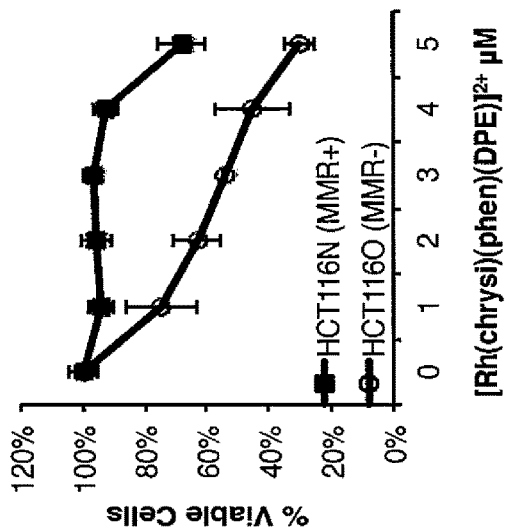
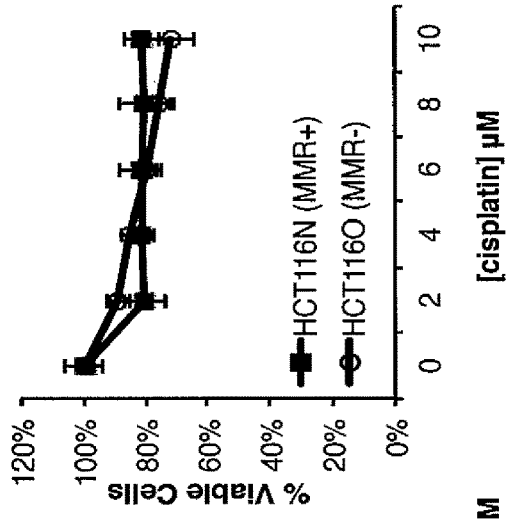
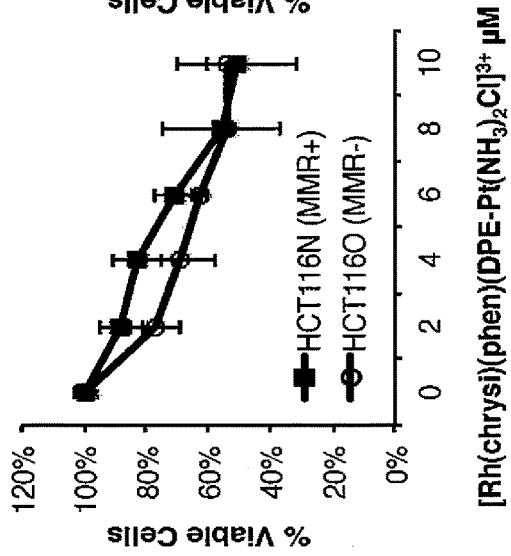

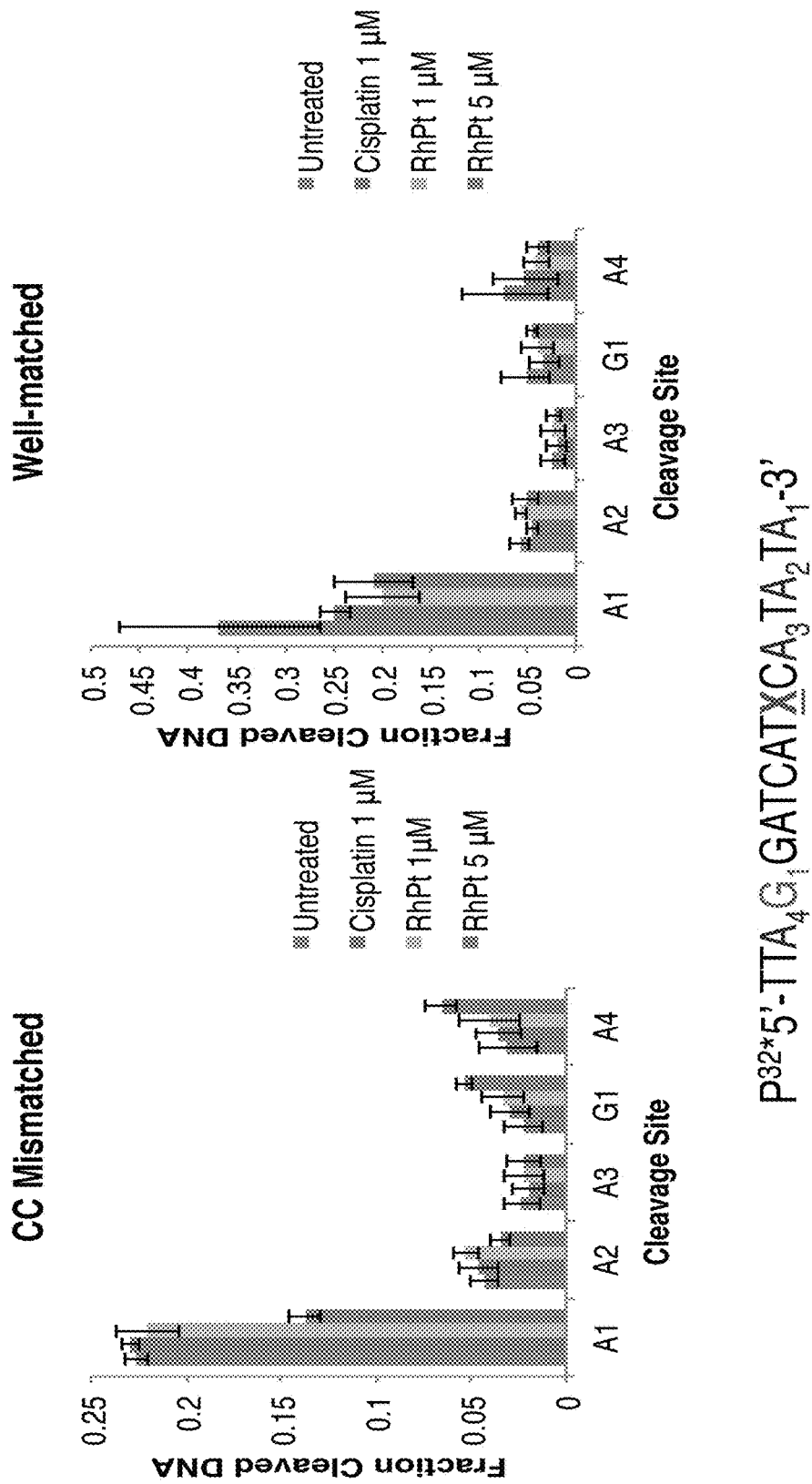

FIG. 24

Cellular Distribution and Cytotoxicity of Complexes in HCT116O Cells

| Complex | Nuclear | Mitochondrial[a] | $LC_{50}$[b] |
|---|---|---|---|
| RhPt | 18 ± 2 µM Pt<br>37 ± 2 µM Rh | 52 ± 13 Pt<br>10 ± 0.4 Rh | 9.0 µM |
| Rh(Amal) | 4 ± 1 µM | 9.8 ± 0.9 | 43.3 µM |
| Pt(Amal) | 13 ± 1 µM | 54 ± 5 | 57.2 µM |
| Oxaliplatin | 15 ± 2 µM | 68 ± 2 | 27.5 µM |
| Cisplatin | 14 ± 2 µM | 73 ± 17 | 29.5 µM |

SEQUENCE LISTING

```
<160> NUMBER OF SEQ ID NOS: 2

<210> SEQ ID NO 1
<211> LENGTH: 29
<212> TYPE: DNA
<213> ORGANISM: Artificial Sequence
<220> FEATURE:
<223> OTHER INFORMATION: 29mer DNA hairpin

<400> SEQUENCE: 1
ggcaggcatg gcttttgcc atccctgcc                                    29

<210> SEQ ID NO 2
<211> LENGTH: 17
<212> TYPE: DNA
<213> ORGANISM: Artificial Sequence
<220> FEATURE:
<223> OTHER INFORMATION: ssDNA oligomer

<400> SEQUENCE: 2
ttaggatcat ccatata                                                17
```

METALLOINSERTOR CONJUGATES

CROSS-REFERENCE TO RELATED APPLICATION(S)

The present application claims priority to and the benefit of U.S. Provisional Application Ser. No. 62/109,474 filed on Jan. 29, 2015, and U.S. Provisional Application Ser. No. 62/111,563 filed on Feb. 3, 2015, the entire contents of both of which are incorporated herein by reference.

STATEMENT REGARDING FEDERALLY SPONSORED RESEARCH OR DEVELOPMENT

This invention was made with government support under Grant No. GM033309 awarded by the National Institutes of Health. The government has certain rights in the invention.

INCORPORATION BY REFERENCE

The instant application contains a Sequence Listing which has been submitted in ASCII format via eFS-Web and is hereby incorporated by reference in its entirety. Said ASCII copy, was created on Apr. 18, 2016, is named 79824SEQLIST.txt, and is 610 bytes in size.

FIELD

This disclosure is directed to metalloinsertor complexes and the use of these complexes to selectively target specific deficient cells.

BACKGROUND

Platinum anticancer agents comprise an essential component in the current repertoire of chemotherapeutics. Cisplatin and carboplatin have been used to successfully treat testicular, cervical, ovarian, and non-small cell lung cancers. However, cancers that exhibit deficiencies in the DNA mismatch repair (MMR) machinery are largely resistant to cisplatin treatment, as MMR proteins are among those responsible for the recognition of Pt-DNA lesions. MMR-deficient cancers, including 15% of sporadic colorectal cancer cases and 18% of all solid tumors, can be treated in part with oxaliplatin, which employs a trans 1,2-diaminocyclohexane non-leaving group ligand instead of the amines. As a result, oxaliplatin-DNA adducts are poorly recognized by MMR proteins, rendering the drug highly effective against cisplatin-resistant cancers in vitro. However, the efficacy of oxaliplatin in vivo is severely limited, and treatment must be administered in combination with a variety of drugs, such as 5-fluorouracil and leucovorin. Although this combinatorial approach does increase the response rate of oxaliplatin treatment, the improvement is modest, and the overall efficacy in the later stages of colorectal cancer is still very low.

Bulky, octahedral rhodium (III) complexes, called metalloinsertors, bind DNA specifically at lesions containing base pair mismatches. This selectivity is achieved through metalloinsertion, a general binding mode in which a sterically expansive ligand inserts into the base stack at the site of the thermodynamically destabilized mismatch, ejecting the mismatched bases from the duplex. As this recognition event occurs with high affinity and over 1000 fold selectivity, metalloinsertors offer a promising alternative in the treatment of MMR-deficient cancers.

SUMMARY

Embodiments of the present invention are directed to a metalloinsertor complex capable of specifically targeting MMR-deficient cells.

In some embodiments of the present invention, a composition includes a complex represented by Formula I, depicted below.

$$M^{m+}(L_1)(L_2)(L_3)(L_4)(L_5)$$ Formula I.

In Formula I, M is rhodium, and m is 2 or 3. $L_1$ is chrysene-5,6-diimine (chrysi), as depicted below:

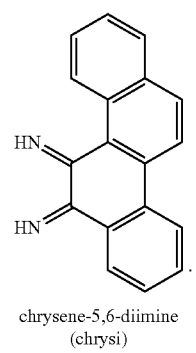 [SMILES: N=C1C(=N)c2c(ccc3ccccc23)-c2ccccc21]

chrysene-5,6-diimine (chrysi)

In Formula I, each of $L_2$ and $L_3$ are adjacent each other, and $L_2$ and $L_3$ combine to form a first single ligand with two coordination sites to M. $L_4$ and $L_5$ are adjacent each other, and $L_4$ and $L_5$ combine to form a second single ligand with two coordination sites to M, the first single ligand and the second single ligand are different, and each of the first and second single ligands is independently selected from the group consisting of:

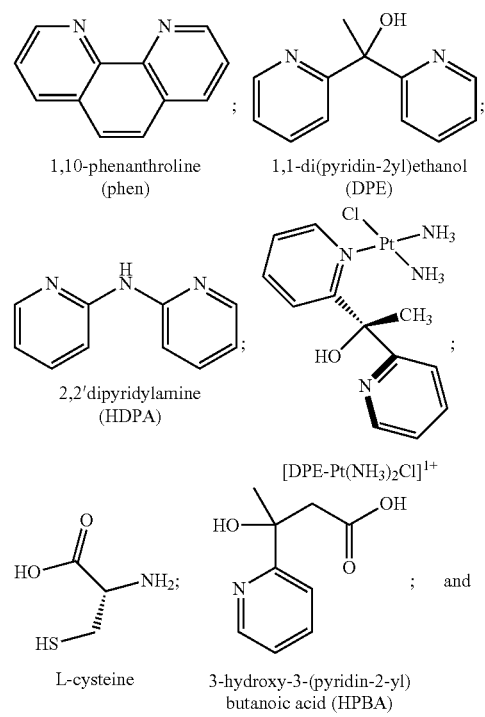

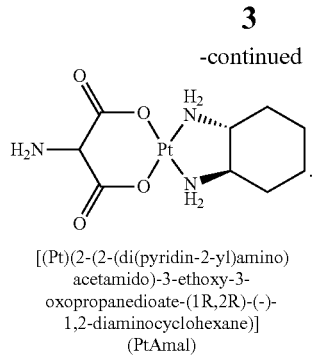

[(Pt)(2-(2-(di(pyridin-2-yl)amino)
acetamido)-3-ethoxy-3-
oxopropanedioate-(1R,2R)-(-)-
1,2-diaminocyclohexane)]
(PtAmal)

In some embodiments of the present invention, a method for selectively inducing cytotoxicity in mismatch repair (MMR)-deficient cells includes providing a metalloinsertor complex of Formula I to the MMR-deficient cells. Here, a decrease in cell viability in the MMR-deficient cells that does not, or would not, comparably decrease cell viability in MMR-proficient cells, indicates selective cytotoxicity in MMR-deficient cells.

In some embodiments, a method of decreasing MMR-deficient cell proliferation includes providing a metalloinsertor complex of Formula I to MMR-deficient cells.

BRIEF DESCRIPTION OF THE DRAWINGS

The patent or application file contains at least one drawing executed in color. Copies of this patent or patent application publication with color drawings will be provided by the Office upon request and payment of the necessary fee.

These and other features and advantages of the present invention will be better understood by reference to the following detailed description when considered in conjunction with the accompanying drawings.

FIG. 7 shows an upper and a lower autoradiogram with the upper autoradiogram showing the formation of covalent platinum adducts with mismatched and well-matched DNA duplexes at 1 μM as a function of time; and the lower autoradiogram showing the formation of covalent platinum adducts with mismatched and well-matched DNA duplexes at 1 μM as a function of [Rh(chrysi)(phen)(DPE-Pt(NH$_3$)$_2$Cl)]$^{3+}$ concentration, according to embodiments of the present invention.

FIG. 9A is a graph of the amount (%) of viable cells as a function of concentration (μM) of [Rh(chrysi)(phen)(DPE-Pt(NH$_3$)$_2$Cl)]$^{3+}$; FIG. 9B is a graph of the amount (%) of viable cells as a function of concentration (μM) of [cisplatin], and FIG. 9C is a graph of the amount (%) of viable cells as a function of concentration (μM) [Rh(chrysi)(phen)(DPE)]$^{2+}$, according to embodiments of the present invention.

FIG. 14 includes two comparative graphs showing quantification of DNA (Fraction Cleaved DNA) footprinting by methyl methanesulfonate (MMS) at purine residues (N3-adenine and N7-guanine) as indicated in CC Mismatched (left) and Well-matched (right) radiolabeled DNA of the sequence as shown with DNA that was untreated (blue bars), treated with Cisplatin (1 µm) (red bars), or treated with RhDPE-Pt (here abbreviated RhPt) at 1 µM (green bars) or 5 µM (purple bars), as indicated, according to embodiments of the present invention.

FIG. 24 is a table showing the cellular distribution (nuclear or mitochondrial) and the cytotoxicity (LC$_{50}$) of the indicated complex in HCT116O cells. $^a$Mitochondrial metal content is normalized to mitochondrial protein using BCA analysis, and is expressed as (ng [metal]/mg [mito protein]), and $^b$LC$_{50}$ refers to the concentration at which 50% of HCT116O cells are viable after 72 h treatment, as determined by MTT assay, according to embodiments of the present invention.

DETAILED DESCRIPTION

Figure 1:
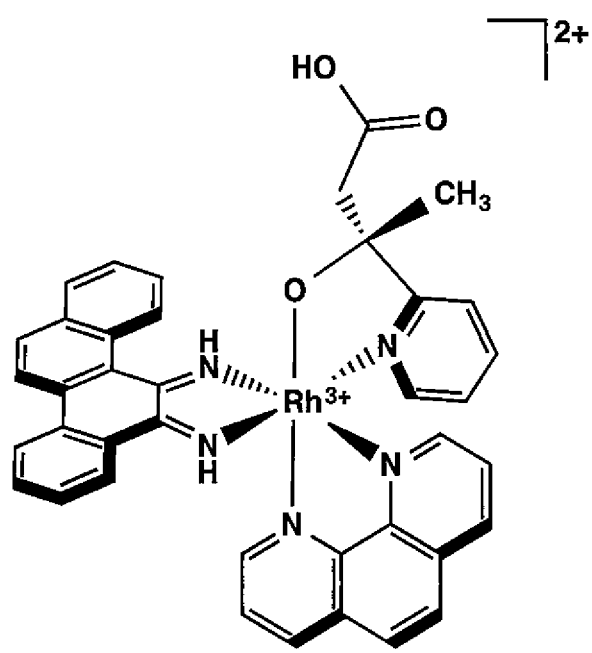
FIG. 1 is the structure of the rhodium metalloinsertor [Rh(chrysi)(phen)(HPBA)]$^{3+}$, according to embodiments of the present invention.
Figure 2:
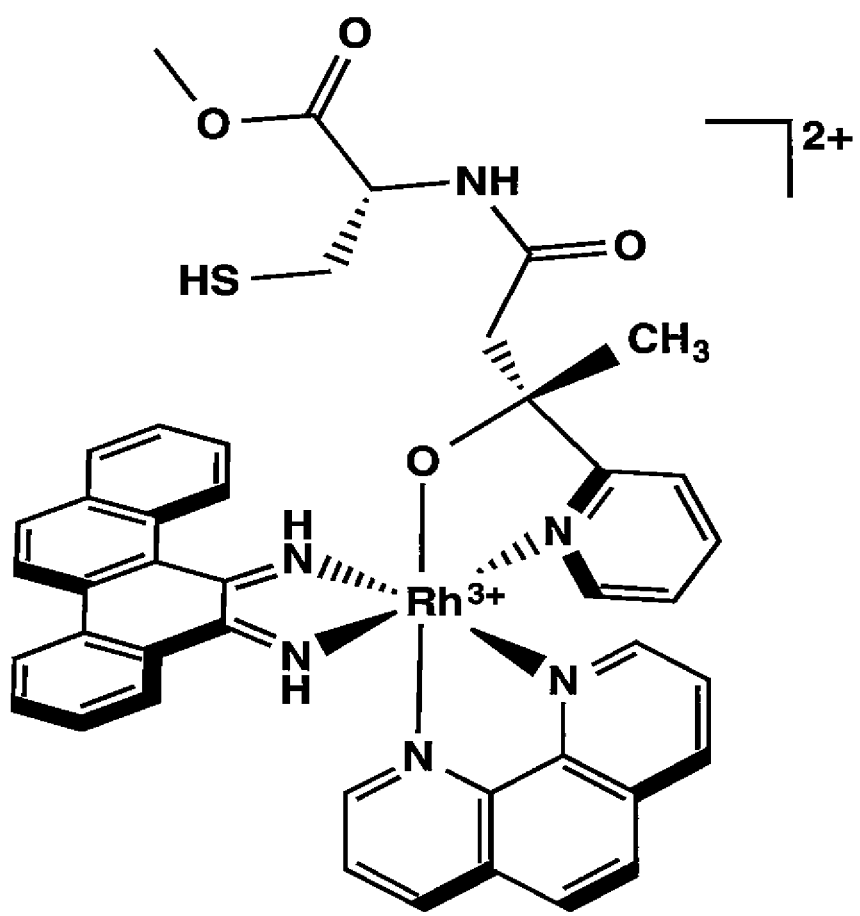
FIG. 2 is the structure of the rhodium metalloinsertor rac-[Rh(chrysi)(phen)(L-cysteine)]$^{3+}$, according to embodiments of the present invention.
Figure 3:
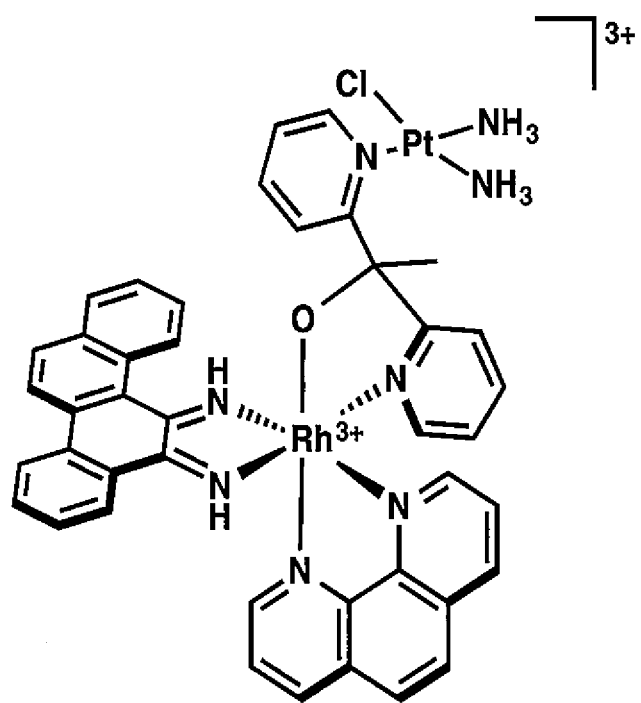
FIG. 3 is the structure of the rhodium metalloinsertor rac-[Rh(chrysi)(phen)(DPE-Pt(NH$_3$)$_2$Cl)]$^{3+}$, according to embodiments of the present invention.
Figure 4:
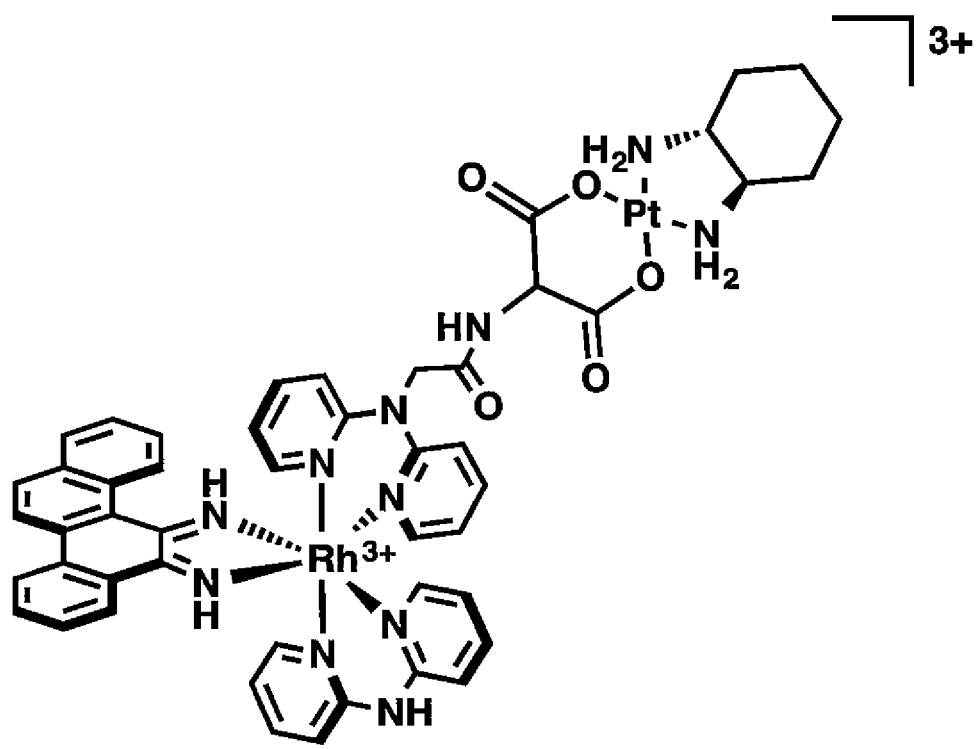
FIG. 4 is the structure of the rhodium metalloinsertor rac-[Rh(chrysi)(HDPA)(Amal)Pt(DACH)]$^{3+}$, according to embodiments of the present invention.
Figure 5:
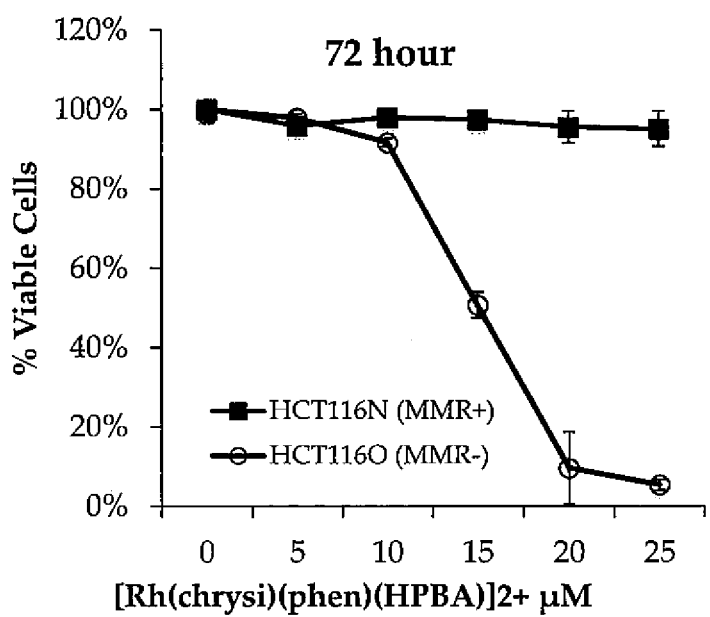
FIG. 5 is a graph of the amount (%) of viable cells as a function of [Rh(chrysi)(phen)(HPBA)]$^{2+}$ concentration in the HCT116N (squares) and the HCT116O (circles) cell lines after a 72 hour incubation, according to embodiments of the present invention.

Rhodium complexes bearing the sterically expansive 5,6-chrysene diimine (chrysi) ligand bind selectively to mismatched sites in duplex DNA in vitro. For example, the x-ray crystal structures of Rh(bpy)$_2$chrysi$^{3+}$ bound to mismatches show a novel insertion binding mode in which the chrysi ligand displaces the mismatched bases from the minor groove. These chrysi complexes of rhodium are capable of selectively inhibiting the cellular proliferation of cells deficient in their mismatch repair (MMR) machinery. Improvements to the design of mismatch specific rhodium complexes include reducing potential steric interactions using smaller ancillary ligands, improving the mismatch binding affinity through modification of the inserting ligand, and optimizing the scaffold for cellular uptake and conjugate development.

Furthermore, despite their lack of selectivity, platinum (II) anticancer agents are still the most successful and most widely used chemotherapeutic agents to date. The ability to tune platinum therapeutics to target specific biomarkers of cancer would be invaluable in the development of next-generation platinum drugs. To this end, Rh—Pt metalloinsertor conjugates according to embodiments of the present invention are disclosed that target platinum to MMR-deficient cells.

It is to be understood that unless otherwise indicated, this disclosure is not limited to specific reactants, reaction conditions, ligands, metal complexes, or the like, as such may vary. It is also to be understood that the terminology used herein is for the purpose of describing particular embodiments only and is not intended to be limiting.

In this specification and in the claims that follow, reference will be made to a number of terms, which shall be defined to have the following meanings:

The terms "compounds of Formula I" and "metalloinsertor complexes" are used interchangeably and all of these terms refer to a complex represented by Formula I as described above and throughout.

Also, as used herein, unless otherwise indicated, the term "rhodium complex" refers to a complex of Formula I in which M is rhodium (Rh).

The term "chrysi" refers to bidentate ligand 5,6-chrysene quinone diimine.

The term "DPE" refers to 1,1-di(pyridin-2-yl)ethanol. The term "DPE complex" or "DPE" to denote a complex, refers to a rhodium complex having a DPE ligand.

The term "bpy" refers to 2,2'-bipyridine. The term "bpy complex" or "bpy" to denote a complex, refers to a rhodium complex having a bpy ligand.

The term "phen" refers to 1,10-phenanthroline. The term "phen complex" or "phen" to denote a complex, refers to a rhodium complex having a phen ligand.

The term "HDPA" refers to 2,2'dipyridylamine. The term "HDPA complex" or "HDPA" to denote a complex, refers to a rhodium complex having a HDPA ligand.

The term "HPBA" refers to 3-hydroxy-3-(pyridin-2-yl) butanoic acid. The term "HPBA complex" or "HPBA" to denote a complex, refers to a rhodium complex having a HPBA ligand.

The term DPE-Pt refers to 1,1-di(pyridin-2-yl)ethanol complexed with platinum (Pt). The term "DPE-Pt complex" or "DPE-Pt" to denote a complex refers to a rhodium complex having a DPE-Pt ligand.

The term "DACH" refers to (1R,2R)-(−)-1,2-diaminocyclohexane).

The terms "aminomalonate" and "Amal" refer to 2-(2-(di(pyridin-2-yl)amino)acetamido)-3-ethoxy-3-oxopropanedioate.

The terms "Pt(Amal)" and "PtAmal" as used herein refer to a complex of Pt(DACH)(Amal).

The terms "L-cysteine" and "L-cys" refer to the L enantiomer of the amino acid cysteine.

The term "rac" refers to racemic mixtures of delta and lambda enantiomers.

Embodiments of the present invention are directed to rhodium (Rh) metalloinsertor complexes that target DNA mismatch and selectively induce cytotoxicity. In some embodiments of the present invention, methods for identifying DNA mismatch include the use of a metalloinsertor complex as described herein. Methods of embodiments of the present invention include using a metalloinsertor complex as described herein for selectively inducing cytotoxicity. Methods of embodiments of the present invention include using a metalloinsertor complex as described herein for selectively decreasing cell proliferation.

In some embodiments of the present invention, a metalloinsertor complex that targets DNA mismatch is represented by Formula I.

$$M^{m+}(L_1)(L_2)(L_3)(L_4)(L_5)$$ Formula I

In Formula I, M is rhodium and m is 2 or 3. $L_1$ is chrysene-5,6-diimine (chrysi), as depicted below.

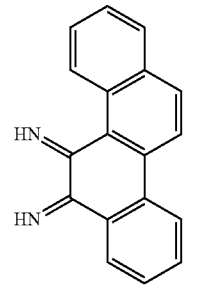

chrysene-5,6-diimine (chrysi)

In Formula I, each of $L_2$ through $L_5$ combines with an adjacent one of $L_2$ through $L_5$ to form two single ligands with two coordination sites to M, where each of the single ligands with two coordination sites to M is selected from:

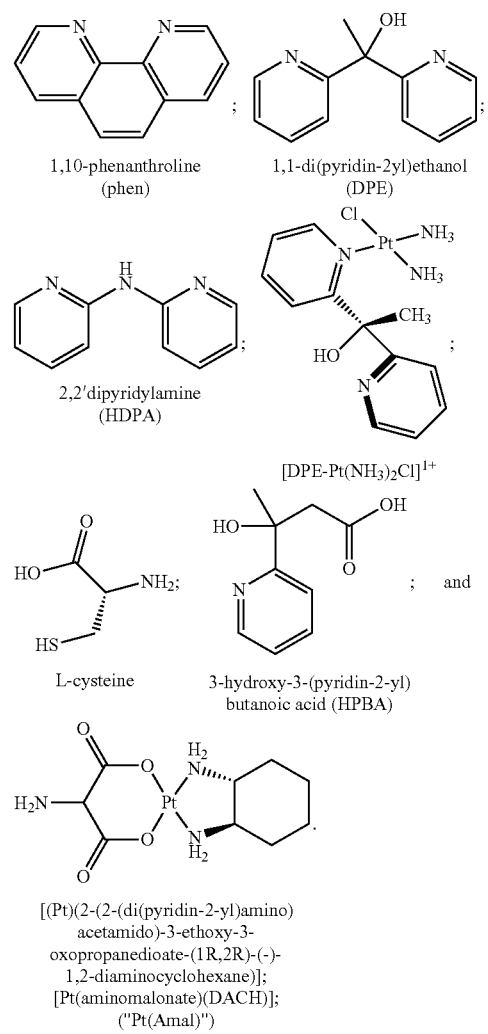

1,10-phenanthroline (phen)

1,1-di(pyridin-2yl)ethanol (DPE)

2,2'dipyridylamine (HDPA)

[DPE-Pt(NH₃)₂Cl]¹⁺

L-cysteine 3-hydroxy-3-(pyridin-2-yl) butanoic acid (HPBA)

; and

[(Pt)(2-(2-(di(pyridin-2-yl)amino) acetamido)-3-ethoxy-3-oxopropanedioate-(1R,2R)-(−)-1,2-diaminocyclohexane)]; [Pt(aminomalonate)(DACH)]; ("Pt(Amal)")

In some embodiments of the present invention, $L_2$ through $L_5$ in Formula I form two single ligands with two coordination sites to M, where each of the single ligands with two coordination sites to M is selected from phen, DPE, DPE-Pt(NH₃)₂Cl, HDPA, HPBA, L-cysteine, and Pt(Amal). These single ligands allow for conjugation of antibodies, carbohydrates or peptides to thereby increase cellular accumulation, specificity and/or biological activity.

Non-limiting examples of suitable metalloinsertor complexes satisfying Formula I include [$M^{m+}$(chrysi)(phen)(HPBA)], [$M^{m+}$(phen)(chrysi)(DPE-Pt(NH$_3$)$_2$Cl)], [$M^{m+}$(chrysi)(HDPA)(Amal)(Pt)(DACH)], and [$M^{m+}$(chrysi)(phen)(L-Cysteine)]. In these examples, M is Rh, and m is 2 or 3.

Some non-limiting examples of suitable metalloinsertor complexes include [Rh(chrysi)(phen)(HPBA)]$^{2+}$, [Rh(chrysi)(phen)(L-cysteine)]$^{2+}$, [Rh(chrysi)(phen)(DPE-Pt(NH$_3$)$_2$Cl)]$^{3+}$, and [Rh(chrysi)(HDPA)(Amal)(Pt)(DACH)]$^{3+}$, as shown in FIGS. 1-4. Synthesis of the complexes are described below.

The metalloinsertor complexes of Formula I according to embodiments of the present invention, accelerate cellular uptake compared to other metalloinsertor complexes, and therefore trigger a selective cytotoxic effect as a function of mismatch repair (MMR) status. Accordingly, the metalloinsertor complexes are not only useful for indicating the presence of polynucleotide damage or error, and diagnosing conditions characterized by polynucleotide damage or error, but are also useful for inducing selective cytotoxicity in cells characterized by polynucleotide damage or error such as cancer cells.

In some embodiments of the present invention, a method of selectively inducing cytotoxicity in an MMR-deficient cell includes providing a metalloinsertor complex of Formula I to an MMR-deficient cell.

The metalloinsertor complexes according to embodiments of the present invention, selectively decrease cell proliferation. As such, a method for selectively decreasing cell proliferation in MMR-deficient cells includes providing a metalloinsertor complex of Formula I to the MMR-deficient cells. This method of selectively decreasing cell proliferation may be in vitro or in vivo. For example, decreasing cell proliferation in vitro may include growing an MMR-deficient cell in the presence of a metalloinsertor complex of Formula I. Cell culture conditions suitable for the selected MMR-deficient cell line are known and discussed below. Decreasing cell proliferation in vivo may include providing or administering a metalloinsertor complex of Formula I to an animal or human.

In embodiments of the present invention, metalloinsertor complexes of Formula I selectively induce cytotoxicity in MMR-deficient cells. A method for selectively inducing cytotoxicity may include providing a metalloinsertor complex of Formula I to MMR-deficient cells. This method of selectively inducing cytotoxicity may be in vitro or in vivo. For example, selectively inducing cytotoxicity in vitro may include growing an MMR-deficient cell in the presence of a metalloinsertor complex of Formula I. Selectively inducing cytotoxicity in vivo may include providing or administering a metalloinsertor complex of Formula I to an animal or human.

In some embodiments of the present invention, a complex of Formula I may be administered orally or parenterally, for example by injection, inhalation, transdermally, or the like, and may be administered in vivo or ex vivo. For example, one can use compounds of the invention to purge bone marrow of tumor cells prior to reintroducing the marrow into a patient (e.g., after radiotherapy). The compounds can be administered systemically or locally, for example via indwelling catheter, controlled- or sustained-release implant, minipump, or the like. Alternatively, the compounds can be formulated as an aerosol, and administered to the lungs and trachea.

The compounds can be formulated in a liquid dosage form such as, for example, liquids, suspensions or the like, preferably in unit dosage forms suitable for single administration of precise dosages. Liquid dosages may be administered by injection or infusion, as nose drops or as an aerosol. The active compound can be prepared as a cream or an ointment composition and applied topically. Delivery may occur by controlled release of these agents by encapsulation either in bulk or at a microscopic level using synthetic polymers, such as silicone, and natural polymers such as gelatin and cellulose. The release rate can be controlled by proper choice of the polymeric system used to control the diffusion rate. Natural polymers, such as gelatin and cellulose slowly dissolve in a matter of minutes to hours while silicone remains intact for a period of months. The compositions may include a conventional pharmaceutical carrier or excipient, in addition to one or more of the active compound(s). In addition, the compositions may include other medicinal agents, pharmaceutical agents, carriers, adjuvants, etc.

The amount of compound administered is of course dependent on the subject being treated, the severity of the affliction, the manner of administration, the frequency of administration, and the judgment of the prescribing physician. Suitable concentrations to determine the "effective amount" can be determined by one of ordinary skill in the art, using only routine experimentation. The frequency of administration is desirably in the range of an hourly dose to a monthly dose, for example, from 8 times/day to once every other day, or 1 to 3 times per day. Ointments containing one or more active compounds and optional pharmaceutical adjuvants in a carrier, such as, for example, water, saline, aqueous dextrose, glycerol, ethanol, and the like, can be prepared using a base such as, for example, petroleum jelly, lard, or lanolin.

Liquified pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. The preparation can additionally contain compounds that facilitate entry of the nucleic acid of interest into the inner ear cells such as Lipofectin, permeability-enhancing agents (e.g., detergents), or other transformation-enhancing agents. Actual methods of preparing such dosage forms are known, or will be apparent, to those skilled in this art. The composition or formulation to be administered will, in any event, contain a quantity of one or more of the active compound(s) in an amount effective to alleviate the symptoms of the subject being treated.

For aerosol administration, the active ingredient may be supplied in finely divided form along with a surfactant and a propellant. Example percentages of active ingredients are 0.001 to 2% by weight, or 0.004 to 0.10%.

Selected surfactants may be nontoxic and soluble in the propellant. Non-limiting examples of these include esters or partial esters of fatty acids containing from 6 to 22 carbon atoms, such as caproic, octanoic, lauric, palmitic, stearic, linoleic, eleostearic and oleic acids with an aliphatic polyhydric alcohol or its cyclic anhydride such as, for example, ethylene glycol, glycerol, erythritol, arabitol, mannitol, sorbitol, and hexitol anhydrides derived from sorbitol (the sorbitan esters are also referred to as "Span®" (Sigma Aldrich) and the polyoxyethylene and polyoxypropylene derivatives of these esters. Mixed esters, such as mixed or natural glycerides, may be employed. The preferred surface-active agents are the oleates orbita, e.g., those sold under the trademarks "Arlacel® C" (sorbitan sesquioleate), "Span® 80" (sorbitan monoleate) (Sigma Aldrich) and "Span® 85" (sorbitan trioleate) (Sigma Aldrich). The surfactant may constitute 0.1 to 20% by weight of the composition, for example 0.25-5% by weight.

The balance of the composition may be propellant. Liquefied propellants may include gases at ambient conditions, and may be condensed under pressure. Non-limiting examples of suitable liquefied propellants include the lower alkanes containing up to five carbons, such as butane and propane; fluorinated or fluorochlorinated alkanes, such as these are sold under the trademark Freon® (Chemours). Mixtures of the above propellants may also be employed.

In producing the aerosol, according to embodiments of the present invention, a container equipped with a suitable valve may be filled with the appropriate propellant, and contain the finely divided active ingredient and surfactant. The ingredients may thus be maintained at an elevated pressure until released by action of the valve.

The following Examples are presented for illustrative purposes only, and do not limit the scope or content of the present application.

EXAMPLES

In the below examples, the following materials are used, unless otherwise indicated. Cisplatin, oxaliplatin, and all organic reagents were purchased from Sigma-Aldrich (St. Louis, Mo.) unless otherwise noted. Commercially available chemicals were used as received without further purification. $RhCl_3$ and $K_2PtCl_4$ starting material were purchased from Pressure Chemical Co. Sep-pak $C_{18}$ solid-phase extraction (SPE) cartridges were purchased from Waters Chemical Co. (Milford, Mass.). Media and supplements were purchased from Invitrogen (Carlsbad, Calif.). BrdU, antibodies, and buffers were purchased in kit format from Roche Molecular Biochemical (Mannheim, Germany). Oligonucleotides were ordered from Integrated DNA Technologies and purified by HPLC using a C18 reverse-phase column (Varian, Inc; Corona, Calif.). All HPLC purifications were carried out on a Hewlett-Packard 1100 HPLC. DNA purity was confirmed by MALDI-TOF mass spectrometry and quantified by UV-vis using the extinction coefficients at 260 nm estimated for single-stranded DNA. UV-vis characterizations were performed on a Beckmann DU 7400 spectrophotometer. Radiolabeled [32P]-ATP was purchased from MP Biomedicals (Santa Ana, Calif.).

The syntheses of chrysene-5,6-dione (chrysi), [Pt(DACH)($H_2O$)$_2$]SO$_4$ (DACH=(1R,2R)-(−)-1,2-diaminocyclohexane), and di(pyridin-2-yl)glycine (dpa-AcOH) were carried out according to published procedures as described in Mürner et al., *Inorg. Chem.* 1998, 37, 3007-3012; Gandolfi et al., *Inorg. Chim. Acta*, 1987, 135, 27-31; and Kirin et al., *Eur. J. Inorg. Chem.*, 2007, 23, 3686-3694, the entire contents of all of which are herein incorporated by reference. The synthesis of precursor [Rh(chrysi)(HDPA)(NH$_3$)$_2$]TFA$_3$ was carried out in a manner analogous to that of [Rh(chrysi)(phen)(NH$_3$)$_2$], as described by Mürner et al, supra.

Example 1. Synthesis of HPBA:
3-hydroxy-3-(pyridin-2-yl)butanoic acid

The carboxylate-modified pyridyl ethanol scaffold ligand was prepared from 2-(pyridin-2-yl)pent-4-en-2-ol.[34, 35] A 50-ml round-bottomed flask was charged with 2-(pyridin-2-yl)pent-4-en-2-ol (202.9 mg, 1.22 mmol), sodium periodate (2.664 g, 12.4 mmol, 10 equiv.), and RuCl$_3$.H$_2$O (39 mg, 0.188 mmol, 0.15 equiv.). The solids were suspended in a biphasic mixture of H$_2$O/MeCN/CH$_2$Cl$_2$ (1.5:1:1, 35 ml) and stirred at ambient temperature for 24 h. An off-white byproduct precipitated out of the reaction mixture, which was removed by filtration and discarded. The filtrate was partitioned between water and CH$_2$Cl$_2$, and extracted with CH$_2$Cl$_2$ (3×30 ml). The product remained in the aqueous phase, and the solution was dried in vacuo. The resulting brown residue was resuspended in diethyl ether, filtered, and washed with ethanol. The filtrate was dried in vacuo to afford the carboxylic acid as a red, crystalline solid. $^1$H NMR (300 MHz, CDCl$_3$): δ 8.51 (d, 1H), 7.81 (t, J=7.7 Hz, 1H), 7.54 (d, J=8.0 Hz, 1H), 7.35-7.25 (m, 1H), 2.95 (s, 2H), 2.58 (s, 1H) 1.61 (s, 3H). ESI-MS (cation): m/z calc 181.07, obs. 182.0 (M+H$^+$).

Example 2. Synthesis of [Rh(chrysi)(phen)(HPBA)]$^{2+}$

A 250 ml round-bottomed flask was charged with [Rh(chrysi)(phen)(NH$_3$)$_2$]TFA$_3$ (50 mg, 0.055 mmol) and 3-hydroxy-3-(pyridin-2-yl)butanoic acid (11 mg, 0.061 mmol, 1.1 equiv). A 1:10 mixture of H$_2$O and EtOH (100 ml) was added, and the solution was heated to reflux. After 18 h, the solution was dried in vacuo and purified by reverse-phase HPLC (85:15:0.1→35:65:0.1 H$_2$O/MeCN/TFA gradient). For biological experiments, the complex was converted to the chloride salt via passage through a QAE Sepharose anion exchange column (0.1 M MgCl$_2$). Yield: 15 mg (29%). ESI-MS (cation): m/z calc 719.605, obs. 720.9.

Example 3. Synthesis of [Rh(chrysi)(phen)(L-cys)]$^{2+}$ 2 mg, (0.002 mmol), (dimethylamino)-N,N-dimethyl(3H-[1,2,3]triazolo[4,5-b]pyridin-3-yloxy)methaniminium hexafluorophosphate (HATU, 7 mg, 0.02 mmol), and L-cysteine methyl ester (7 mg, 0.04 mmol) were added to a 25 ml round-bottomed flask and dried under vacuum to remove all water. The solids were dissolved in 0.8 ml dimethylformamide (DMF) under argon, and Ethyldiisopropylamine (DIPEA, 20 µl, 0.12 mmol) was added dropwise. After 18 h stirring at ambient temperature, the mixture was dried in vacuo, redissolved in water, and purified by reverse-phase HPLC (85:15:0.1→35:65:0.1 H$_2$O/MeCN/TFA gradient). ESI-MS (cation): m/z calc 836.164, obs. 836.2.

Example 4

Syntheses of chrysene-5,6-dione (chrysi), 1,1-di(pyridin-2-yl)ethanol (DPE), and [Rh(chrysi)(phen)(DPE)]$^{2+}$ were carried out according to published procedures, as described in Komor et al., *J. Am. Chem. Soc.* 2012, 134, 19223-19233; Basu et al., *J. Chem. Soc., Chem Commun.* 1987, 22, 1724-1725; and Muerner et al., *Inorg. Chem.* 1998, 37, 30007-3012, the entire contents of all of which are herein incorporated by reference.

Example 5. Synthesis of [Rh(chrysi)(phen)(DPE-Pt(NH$_3$)$_2$Cl)]Cl$_3$

A 250 ml round bottomed flask was charged with [Rh(chrysi)(phen)(DPE)]TFA$_2$ (272 mg, 0.28 mmol) (prepared according to Komor et al., 2012, supra) and cisplatin (305 mg, 1 mmol, 3.57 equiv) in 100 ml H₂O. One drop of concentrated HCl was added, and the solution was stirred at reflux for an additional 48 h. The reaction was hot-filtered through a medium glass frit and purified by reverse-phase HPLC (85:15:0.1 to 40:60:0.1 H₂O/MeCN/TFA gradient). Fractions were pooled and dried in vacuo to afford the bimetallic product as a red-brown solid. To obtain the complex as the chloride salt, [Rh(chrysi)(phen)(DPE-Pt(NH$_3$)$_2$Cl]TFA$_3$ was redissolved in 50 mM HCl$_{(aq)}$ and freeze-dried under high vacuum. This process was repeated three times until the TFA counterion was eliminated. Yield: 60 mg (16% by HPLC). ¹H NMR (500 MHz, D₂O): δ 9.39 (d, J=5.3 Hz, 1H), 8.95 (d, J=8.0 Hz, 1H), 8.90 (d, J=6.7 Hz, 2H), 8.87-8.68 (m, 1H), 8.49-8.35 (m, 1H), 8.34-8.27 (m, 1H), 8.24-8.18 (m, 1H), 8.14-8.11 (m, 1H), 8.07 (d, J=10.3 Hz, 1H), 8.03 (s, 1H), 8.00 (d, J=6.7 Hz, 2H), 7.96 (d, J=8.0 Hz, 2H), 7.90 (d, J=7.9 Hz, 1H), 7.81 (s, 1H), 7.72 (d, J=7.5 Hz, 1H) 7.68-7.60 (m, 1H), 7.57 (s, 1H), 7.52 (t, J=7.5 Hz, 1H), 7.41 (s, 2H), 7.32 (d, J=6.8 Hz, 2H), 7.27-7.17 (m, 1H), 7.00 (d, J=7.8 Hz, 1H), 3.66-3.59 (m, 3H), 3.54 (dd, J=5.6, 3.5 Hz, 3H), 2.95 (s, 3H). ESI-MS (cation): m/z calc 1003.251, obs. 1001.8 (M−2H⁺). UV-vis (H₂O, pH 7.0): 270 nm (134,700 M⁻¹ cm⁻¹), 303 nm (72,400 M⁻¹ cm⁻¹), 442 nm (19,200 M⁻¹ cm⁻¹), 581 nm (10,600 M⁻¹ cm⁻¹).

Scheme 1. Synthesis of RhPt (1).

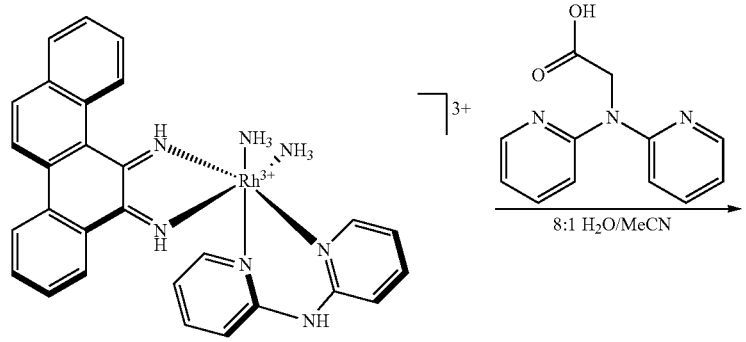

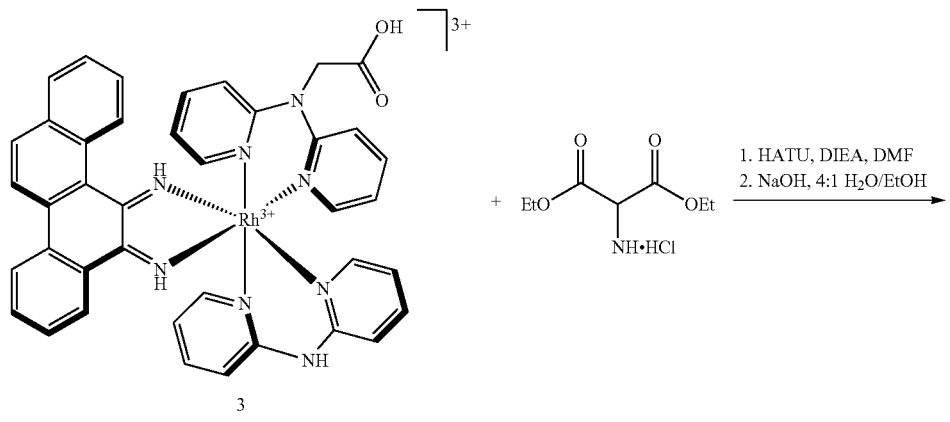

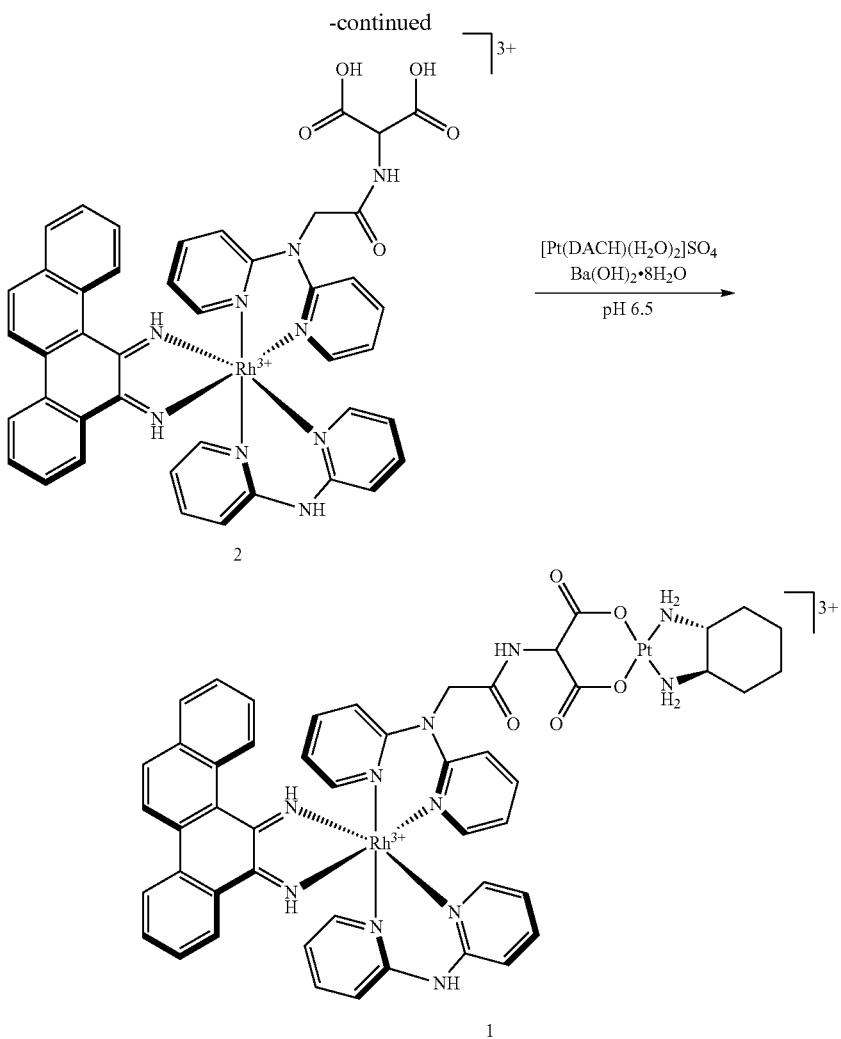

Example 6. Synthesis of "RhPt" [Rh(chrysi)(H-DPA)(Amal)Pt(DACH]$^{3+}$

The synthesis of conjugate RhPt is shown in Scheme 1 below, and was carried out as described below.

Synthesis of [Rh(HDPA)(chrysi)(dpa-AcOH](TFA)$_3$ (3)

[Rh(HDPA)(chrysi)(NH3)$_2$](TFA)$_3$ (4) (620 mg, 0.69 mmol) and di(pyridin-2-yl)glycine (dpa-AcOH) (240 mg, 1.05 mmol) were dissolved in 8:1 H$_2$O:MeCN (90 ml) and refluxed for 24 h. The solvent was removed in vacuo, and the crude product was purified by HPLC using a C$_{18}$ reverse-phase column (Varian, Inc.) on a Hewlett Packard 1100 HPLC (85:15 to 40:60 H$_2$O (0.1% TFA):MeCN). Complex 3 was isolated as a dark red, hygroscopic solid. Yield: 0.55 g (73%). $^1$H NMR (300 MHz, DMSO-d6) δ 11.47 (broad s, 1H), 9.64 (s, 1H), 9.04 (d, J=6.2 Hz, 1H), 8.77 (dd, J=15.0, 6.8 Hz, 1H), 8.52 (d, J=6.1 Hz, 1H), 8.24 (dd, J=5.0, 1.8 Hz, 4H), 8.08 (dt, J=16.7, 9.5 Hz, 2H), 8.01-7.84 (m, 4H), 7.80-7.74 (m, 1H), 7.71 (d, J=8.1 Hz, 1H), 7.67 (s, 1H), 7.56-7.40 (m, 3H), 7.38-7.29 (m, 1H), 7.19 (t, J=8.4 Hz, 4H), 6.99-6.86 (m, 3H), 6.86-6.74 (m, 1H), 4.63 (s, 2H). ESI-MS (cation): m/z calc 757.17 (M-2H$^+$), 379.59 (M-H$^{2+}$), obs. 756.9, 379.1.

Synthesis of [Rh(HDPA)(chrysi)(diethyl-2-(2-(di(pyridin-2-yl)amino)acetamido)malonate] (TFA)$_3$

[Rh(HDPA)(chrysi)(dpa-AcOH](TFA)$_3$ (3) (100 mg, 0.09 mmol), diethyl aminomalonate hydrochloride (38 mg, 0.18 mmol), and (dimethylamino)-N,N-dimethyl(3H-[1,2,3]triazolo[4,5-b]pyridin-3-yloxy)methaniminium hexafluorophosphate (HATU, 83 mg, 0.22 mmol) were combined in a vial and dried under vacuum to remove all water. The solids were dissolved in anhydrous DMF (1.3 ml) under argon and stirred at room temperature for 10 min. Ethyldiisopropylamine (DIPEA, 95 µl, 0.54 mmol) was added, and the solution was allowed to stir at room temperature for 12 h. The solvent was removed in vacuo, and the intermediate was purified by HPLC as described above. Yield: 41 mg (36% by HPLC). ESI-MS (cation): m/z calc 914.24 (M-2H$^+$), 457.12 (M-H$^{2+}$), obs. 913.9, 457.8

Synthesis of [Rh(HDPA)(chrysi)(2-(2-(di(pyridin-2-yl)amino)acetamido)-3-ethoxy-3-oxopropanoic acid)] (TFA)₃ ("Rh(Amal)") (2)

To hydrolyze the ethyl esters, [Rh(HDPA)(chrysi)(diethyl-2-(2-(di(pyridin-2-yl)amino)acetamido)malonate] (TFA)₃ (41 mg, 0.033 mmol) was dissolved in a 5:1 H₂O:EtOH mixture (12 ml). 1N NaOH was added to pH 10, and the reaction was stirred at room temperature for 24 h. The solvent was removed by rotary evaporation, and Rh(Amal) was purified by HPLC as described above. The chloride salt was obtained from a Sephadex QAE anion-exchange column equilibrated with 0.1 M MgCl₂. Yield: 12 mg (30% by HPLC). ¹H NMR (500 MHz, D₂O): δ 8.91 (dd, J=6.2, 1.6 Hz, 1H), 8.23-8.15 (m, 1H), 8.14-8.11 (m, 2H), 8.08 (dd, J=13.5, 7.6 Hz, 1H), 8.00 (ttd, J=8.3, 6.9, 1.8 Hz, 3H), 7.94-7.90 (m, 1H), 7.90-7.85 (m, 1H), 7.83 (d, J=7.6 Hz, 1H), 7.79 (d, J=1.7 Hz, 1H), 7.78-7.76 (m, 1H), 7.59 (ddd, J=7.9, 6.5, 1.3 Hz, 1H), 7.51-7.45 (m, 3H), 7.36 (td, J=6.9, 6.3, 1.4 Hz, 2H), 7.34-7.30 (m, 1H), 7.29 (d, J=1.2 Hz, 1H), 7.27 (ddd, J=4.6, 2.4, 1.0 Hz, 1H), 7.26 (q, J=2.2 Hz, 1H), 7.25-7.22 (m, 1H), 7.21-7.17 (m, 1H), 7.11-7.06 (m, 3H), 6.91 (ddd, J=7.7, 6.5, 1.4 Hz, 1H), 4.87 (s, 2H), 3.67 (s, 1H). ESI-MS (cation): m/z calc 858.18 (M−2H⁺), 429.09 (M−H²⁻), obs. 857.7, 429.5. UV-vis (H₂O, pH 7): 259 nm (53,500 M⁻¹ cm⁻¹), 287 nm (39,300 M⁻¹ cm⁻¹), 402 nm (6,400 M⁻¹ cm⁻¹).

Synthesis of "RhPt"

To a solution of Rh(Amal) (12 mg, 0.01 mmol) in H₂O (10 ml) was added aqueous Ba(OH)₂.8H₂O (54 mg, 0.17 mmol in 5 ml H₂O) to pH 11. The yellow suspension was sonicated and added dropwise to a stirred solution of [Pt(DACH)(H₂O)₂]SO₄ (76 mg, 0.17 mmol) in H₂O (10 ml) at ambient temperature. The solution turned orange upon addition of the Ba/Rh mixture, and BaSO₄ crashed out as a white precipitate. The remaining Ba(OH)₂☐H₂O stock was added to the mixture until a pH 7 was reached, and the reaction was allowed to stir at room temperature for 24 h. The BaSO₄ byproduct was filtered, and the filtrate was concentrated in vacuo and purified by HPLC. The chloride salt was obtained from a Sephadex QAE anion-exchange column equilibrated with 0.1 M MgCl₂. Yield: 7.1 mg (57% by HPLC). ¹H NMR (300 MHz, D₂O): δ 10.06 (s, 1H, chrysi NH), 8.19 (d, J=6.9 Hz, 1H, chrysi CH), 8.12 (d, J=13.2 Hz, 1H, chrysi CH), 8.05 (d, J=9.2 Hz, 1H, chrysi CH), 8.00-7.92 (m, 1H, chrysi CH), 7.89 (d, J=10.0 Hz, 1H, chrysi CH), 7.83 (s, 1H, chrysi CH), 7.80 (s, 1H, chrysi CH), 7.74 (s, 1H, CONH), 7.64 (d, J=8.1 Hz, 2H, py), 7.55 (d, 1H, chrysi CH), 7.54-7.47 (m, 2H, py), 7.47-7.33 (m, 1H, chrysi CH), 7.23 (d, J=6.1 Hz, 1H, chrysi CH), 7.13 (dt, J=13.3, 6.5 Hz, 2H, py), 6.97 (dd, J=14.5, 7.1 Hz, 2H, py), 6.42-5.93 (m, 2H, Pt—NH₂), 5.57-5.03 (m, 2H, Pt—NH₂), 2.43 (d, J=1.3 Hz, 2H, dach CH), 1.92 (d, J=10.1 Hz, 1H, dach CH), 1.43 (s, 2H, dach CH), 1.16 (s, 1H, dach CH), 0.99 (t, J=10.2 Hz, 2H, dach CH). ESI-MS (cation): m/z calc 1165.24 (M−2H⁺), 583.12 (M−H²⁺), obs. 1165.9, 582.9. UV-vis (H₂O, pH 7): 315 nm (27,000 M⁻¹ cm⁻¹), 389 nm (5,420 M⁻¹ cm⁻¹).

Example 7. Synthesis of Pt(Amal) (Scheme 2)

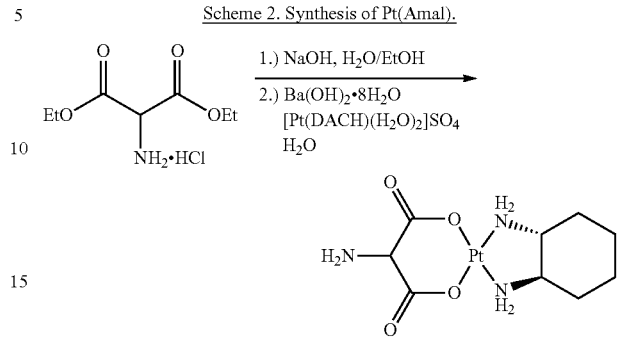

Scheme 2. Synthesis of Pt(Amal).

Synthesis of [Pt(DACH)(aminomalonate)] ("Pt(Amal)"). Diethyl aminomalonate hydrochloride (110 mg, 0.52 mmol) was hydrolyzed in a solution of 4:1 H₂O:EtOH (10 ml) basified with 1N NaOH (pH 13). The reaction was stirred at room temperature overnight, neutralized with 1N HCl, and dried in vacuo to afford the diacid as a white solid. The resulting aminomalonic acid hydrochloride (78 mg, 0.366 mmol) was added to a suspension of Ba(OH)₂.8H₂O (58 mg, 0.183 mmol) in 10 ml H₂O. The mixture was added dropwise to a solution of [Pt(DACH)(H₂O)₂]SO₄ (81 mg, 0.183 mmol) in H₂O (20 ml) and stirred at room temperature, pH 7, for 3 h. The BaSO₄ precipitate was removed by vacuum filtration, and the filtrate was left to stand at 4° C. A yellow precipitate was filtered and dried under vacuum. The residue was dissolved in a minimum volume of water, filtered through Celite, and dried under vacuum again to give Pt(Amal) as a pale yellow solid. Yield: 10 mg (13%). ¹H NMR (300 MHz, D₂O): 3.96 (s, 2H), 3.74 (s, 1H), 2.26 (m, 2H), 1.98 (m, 2H), 1.40 (m, 2H), 1.31 (m, 2H), 0.99 (m, 2H). ESI-MS (cation): m/z calc 426.09, obs. 449.0 (M+Na⁺).

Example 8. PEGylation

Methods for PEGylation for drug delivery are known in the art. For example, Greenwald et al., 2003, *Adv. Drug Del. Rev.*, 55, 217; Molineux, 2003, *Pharmacotherapy*, (8 Pt 2), 3S-8S; Roberts et al., 2002, *Adv. Drug Deliv. Rev.*, 54, 459; and Greenwald, 2001, *J. Controlled Release* 74, 159, the entire contents of all of which are incorporated herein by reference.

Methodology for Metalloinsertor Complex Assays

The metalloinsertor complexes as synthesized and described were assayed in cellulo using the isogenic colorectal carcinoma cell lines HCT116N and HCT116O. The methods used are as follows.

Example 9. Cell Culture

HCT116N (MMR-proficient) and HCT116O (MMR-deficient) cells were grown in RPMI medium 1640 supplemented with 10% fetal bovine serum, 400 μg/ml Geneticin (G418), 2 mM L-glutamine, 0.1 mM nonessential amino acids, 1 mM sodium pyruvate, 100 units/ml penicillin, and 100 μg/ml streptomycin. Cells were grown in tissue culture flasks (Corning Costar, Acton, Mass.) at 37° C. under a humidified atmosphere (5% CO₂).

Example 10. Cellular Proliferation ELISA, as Disclosed in FIGS. 22A, 22B, 22C, and 23

HCT116N and HCT116O cells were plated in 96-well plates at 2000 cells/well and given 24 h to adhere. The cells were incubated with varying concentrations of metal complex (0-2 μM) and grown for an additional 24 hours (h). The media was then replaced with fresh media free of Rh or Pt for the remainder of the 72 h experiment. Cells were labeled with BrdU 24 h before analysis, and BrdU incorporation was quantified by antibody assay, as described in Graztner, *Science,* 1982, 218, 474-475, the entire contents of which are herein incorporated by reference. Cellular proliferation was expressed as the amount of BrdU incorporated into treated cells compared to that of the untreated controls. Errors were calculated from 5 replicates.

Example 11. MTT (3-(4,5-dimethylthiazol-2-yl)-2, 5-diphenyltetrazolium bromide) Cytotoxicity Assay as Disclosed in FIGS. 5, 9A, 9B, 9C, 10A, 10B, 19, and 25

HCT116N and/or HCT116O cells were plated in 96-well plates at 50,000 cells/well and incubated with varying concentrations of metal complex (100 nM-100 μM) for 72 hours. For caspase-inhibition assays, Z-VAD-FMK was added to a final concentration of 20 μM. For poly-ADP ribose polymerase (PARP) assays, the inhibitor 3,4-dihydro-5[4-(1-piperindinyl)butoxy]-1(2H)-isoquinoline (DPQ) was added to a final concentration of either 25 or 50 μM. After the incubation period, cells were labeled with MTT for 4 hours at 37° C., 5% $CO_2$. The ensuing formazan crystals were dissolved with a lysis buffer (10% SDS in 10 mM HCl) according to the manufacturer's instructions, as described in Mosmann, *J. Immunol. Methods,* 1983, 65, 55-63, the entire contents of which are herein incorporated by reference. MTT reduction to formazan was quantified by electronic absorption at 570 nm (background: 690 nm), and percent viability was expressed as the amount of formazan in treated cells compared to that of the untreated controls. Errors were calculated from 5 replicates.

Figure 18A:
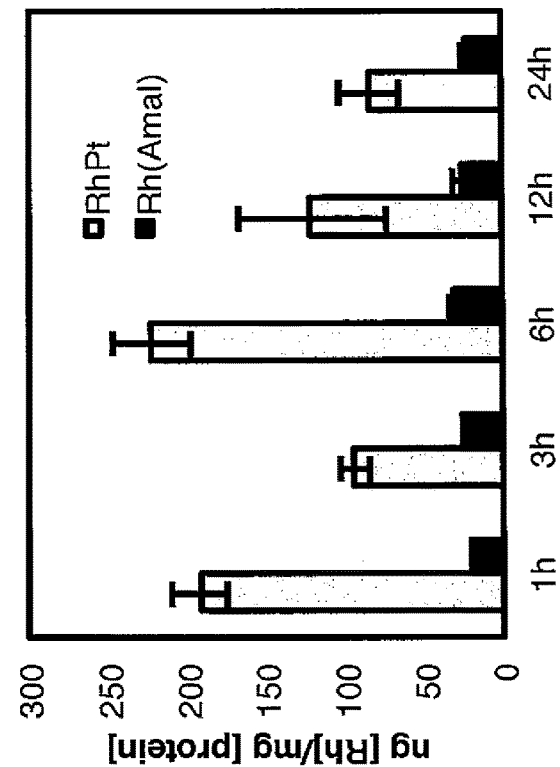
FIG. 18A is a graph of the cellular accumulation of metal complexes (ng [Pt]/mg [protein]) as a function of time (hours) in which HCT116O cells were treated with (bars left to right) of [Rh(chrysi)(HDPA)(Amal)Pt(DACH)]$^{3+}$ (abbreviated RhPT), oxaliplatin, cisplatin, or Pt(Amal), according to embodiments of the present invention.
Figure 18B:
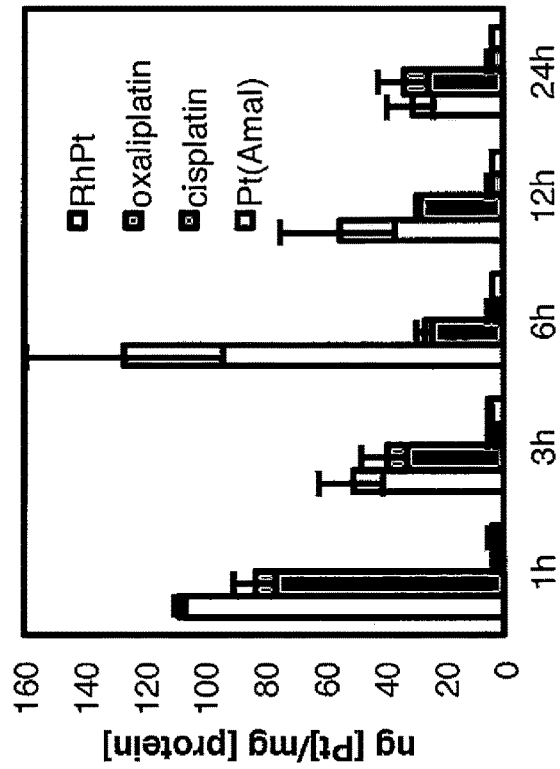
FIG. 18B is a graph of the cellular accumulation of metal complexes (ng [Rh]/mg [protein]) as a function of time (hours) in which HCT116O cells were treated with (bars left to right) of [Rh(chrysi)(HDPA)(Amal)Pt(DACH)]$^{3+}$ (abbreviated RhPT) or Rh(Amal), according to embodiments of the present invention.
Figure 19:
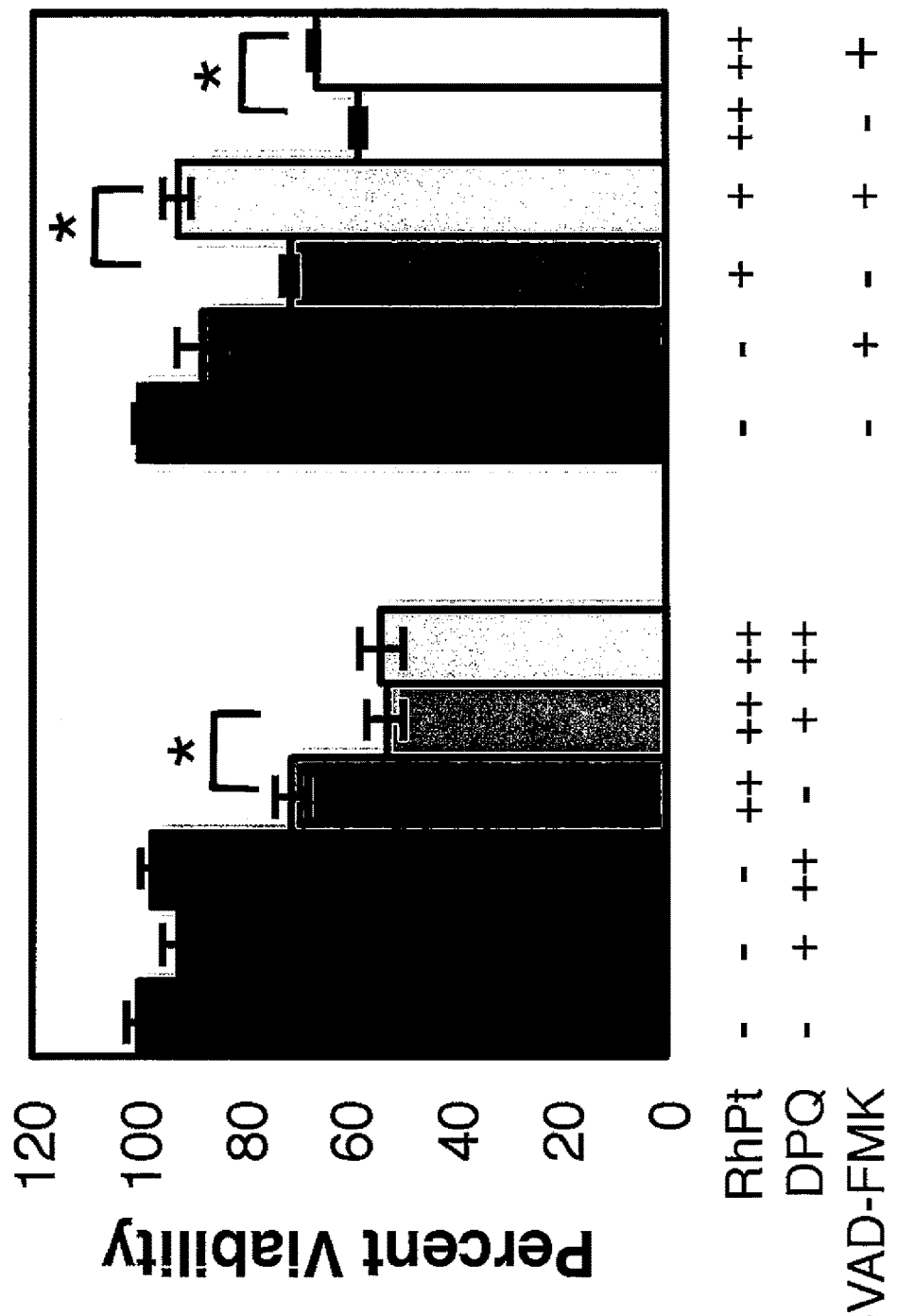
FIG. 19 is a graph showing percent cell viability in HCT116O cells after 72 hours of incubation with (+) or (−) without PARP inhibitor (DPQ), caspase inhibitor (Z-VAD-FMK) and/or of [Rh(chrysi)(HDPA)(Amal)Pt(DACH)]$^{3+}$ (abbreviated RhPT) as indicated, according to embodiments of the present invention.

Example 12. ICP-MS (Inductively Coupled Plasma Mass Spectrometry) Assay for Whole-Cell Rhodium and Platinum, as Disclosed in FIG. 18A and FIG. 18B

HCT116O cells ($1.0 \times 10^6$) were seeded in 6-well plates containing 3 ml media and allowed 24 hours to adhere. The cells were treated with 2 μM of RhPt, Rh(Amal), Pt(Amal), cisplatin, or oxaliplatin and incubated for periods of 1, 3, 6, 12, or 24 hours. After the incubation period, the media was decanted and the wells were washed with 4×5 ml PBS. The cells were lysed with 1 ml of a 1% sodium dodecyl sulfate (SDS) solution and sonicated using a Qsonica Ultrasonic processor for 20 s at 20% amplitude. A 750 μl aliquot was diluted with 750 μl of a 2% $HNO_3$ (v/v) solution and analyzed for rhodium and platinum content on a Thermo X Series II ICP-MS unit. ICP-MS measurements for platinum content were measured only for the three most abundant naturally occurring isotopes, $^{194}Pt$ (33%), $^{195}Pt$ (34%), and $^{196}Pt$ (25%). The remainder of the cell lysate was analyzed for protein content via a bicinchoninic assay (BCA), as described in Smith et al., *Anal. Biochem.* 1985, 150, 76-85, the entire contents of which are herein incorporated by reference. Rhodium and platinum counts were normalized to protein content to obtain ng [Rh/Pt]/mg [protein], and standard errors were calculated from three replicates.

Example 13. ICP-MS for Nuclear Isolation as Disclosed in FIG. 24

Nuclear fractions were isolated from HCT116O cells according to published procedures as described in Komor et al., *J. Am. Chem. Soc.* 2012, 134, 19223-19233 and Weidmann et al., *Philos. Trans. R. Soc. A.,* 2013, 371, 20120117, the entire contents of both of which are herein incorporated by reference. Briefly, $1.0 \times 10^7$ HCT116O cells were harvested by trypsinization and washed with cold phosphate-buffered saline (PBS, pH 7.2). The resulting pellets were resuspended in 1 ml hypotonic buffer (20 mM Tris-HCl, 10 mM NaCl, 3 mM $MgCl_2$, pH 7.4) and incubated at 0° C. for 15 min. NP-40 (50 μl) was added, and the samples were immediately vortexed at high speed for 10 s. The solution was centrifuged at 3,000 g for 10 min, and the pellet was isolated as the nuclear fraction. Nuclear rhodium and platinum concentrations were analyzed by ICP-MS as described above, and normalized to the number of nuclei.

Example 14. ICP-MS Assay for Mitochondrial Isolation as Disclosed in FIG. 24

Mitochondrial fractions were isolated from HCT116O cells as described previously in Komor et al., 2012, supra, and Weidmann et al., 2013, supra. Briefly, $1.5 \times 10^7$ HCT116O cells were harvested by trypsinization and washed with cold PBS. The cell pellets were resuspended in 0.5 ml mitochondrial extraction buffer (200 mM mannitol, 68 mM sucrose, 50 mM pipes, 50 mM KCl, 5 mM EGTA, 2 mM $MgCl_2$, 1 mM DTT, protease inhibitors) and incubated at 0° C. for 20 min. The suspension was homogenized via passage through a 23-gauge needle into a 1-ml syringe (35×). The lysate was centrifuged at 150 g for 5 min. The supernatant was collected and centrifuged at 14,000 g for 10 min, and the resulting pellet was isolated as the mitochondrial fraction. Mitochondrial rhodium and platinum concentrations were analyzed by ICP-MS as described above, and normalized to mitochondrial protein content as determined by BCA analysis.

Example 15. Photocleavage Competition Titrations, as Disclosed in FIGS. 6 and 12

Figure 6:
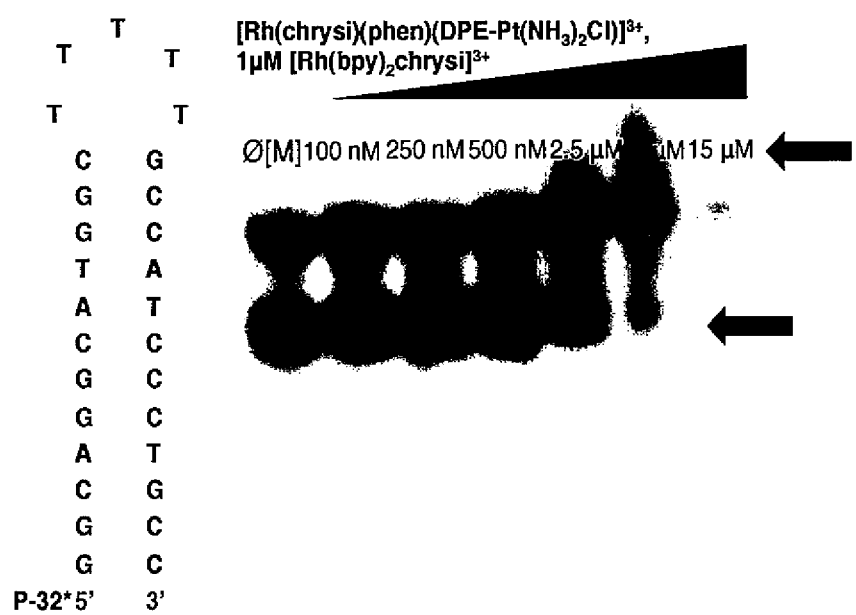
FIG. 6 is an autoradiogram of 20% denaturing polyacrylamide gel showing competition titration of increasing concentrations of [Rh(chrysi)(phen)(DPE-Pt(NH$_3$)$_2$Cl)]$^{3+}$ (0-15 μM as indicated) with 1 μM rac-[Rh(bpy)$_2$chrysi]$^{3+}$ on 1 μM 5'-[$^{32}$P] labeled 29mer hairpin DNA of the sequence indicated containing a CC mismatch with the site of photocleavage by [Rh(bpy)$_2$chrysi]$^{3+}$ at the mismatch indicated by the lower arrow at bands located below the unmodified parent band, according to embodiments of the present invention.
Figure 12:
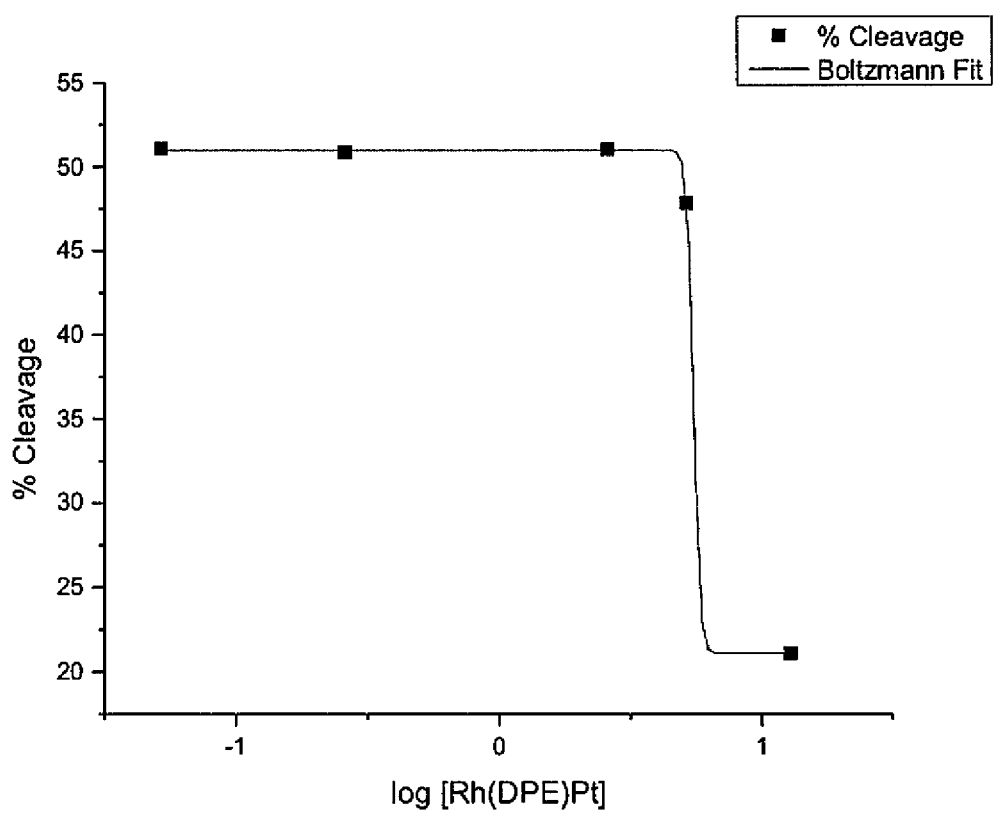
FIG. 12 is a representative sigmoidal curve (Boltzmann fit) of photocleavage competition titrations of [Rh(chrysi)(phen)(DPE-Pt(NH$_3$)$_2$Cl)]$^{3+}$ for binding constant determination at the CC mismatch, according to embodiments of the present invention.

For [Rh(DPE)Pt]$^{3+}$ Conjugate (FIGS. 6 and 12). A 29mer DNA hairpin with the sequence 5'-GGCAGG CATGGCTTTTTGCCATCCCTGCC-3' (SEQ ID NO: 1) (underline denotes the mismatch) was labeled at the 5'-end with [$^{32}$P]-ATP using polynucleotide kinase (PNK) at 37° C. for 2 h followed by purification using gel electrophoresis. A small amount of the labeled DNA (less than 1% of the total amount of DNA) was added to 2 μM DNA in 100 mM NaCl, 20 mM NaP$_i$, pH 7.1 buffer. The DNA hairpin was annealed by heating at 90° C. for 10 min and cooling slowly to ambient temperature over a period of 3 h. Racemic solutions of [Rh(chrysi)(phen)(DPE-Pt(NH$_3$)$_2$Cl)]$^{3+}$ were prepared in Milli-Q water over a range of concentrations (100 nM-50 μM). For each sample, 4 μM rac-[Rh(bpy)$_2$chrysi]Cl$_3$ (5 μl), which photocleaves DNA at mismatched sites, 2 μM annealed mismatched duplex DNA (10 μl), and the non-photocleaving competitor complex at various concentrations (5 μl) were combined to give 1 μM rac-[Rh(bpy)$_2$chrysi]$^{3-}$, 1 μM duplex DNA, and 50 mM NaCl$_{(aq)}$ as the final concentrations. Samples were irradiated on an Oriel (Darmstadt, Germany) 1000-W Hg/Xe solar simulator (340-440 nm) for 15 min, incubated at 37° C. for 10 min, and dried in vacuo. The irradiated samples were electrophoresed on a 20% denaturing polyacrylamide gel and exposed to a phosphor screen. The amounts of DNA in each band were analyzed by autoradiography and quantitated by phosphorimagery (ImageQuant).

Example 16. Photocleavage Competition Titrations, as Disclosed in FIGS. 17 and 20

Figure 17:
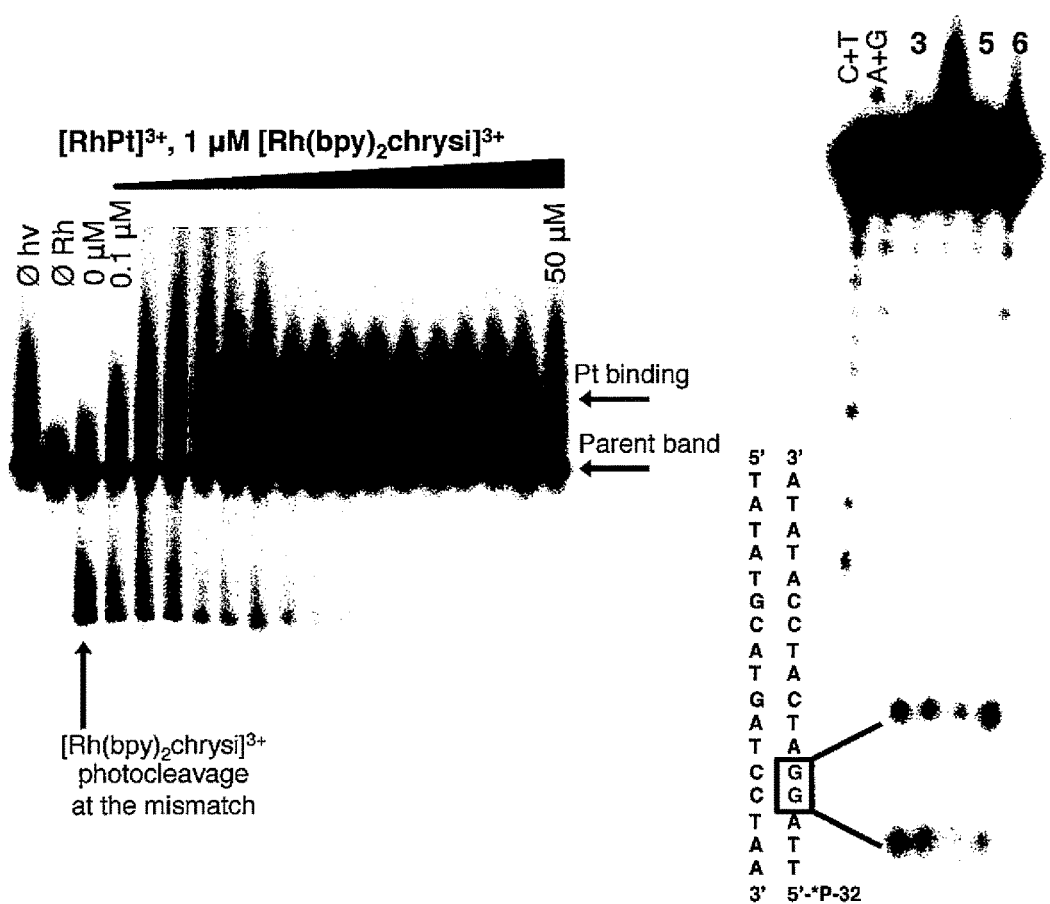
FIG. 17 shows DNA binding of [Rh(chrysi)(HDPA)(Amal)Pt(DACH)]$^{3+}$ (abbreviated RhPT), according to embodiments of the present invention. On the left is an autoradiogram of 20% denaturing polyacrylamide gel showing a competition titration of increasing concentrations of [RhPt] (0-50 µM as indicated) with 1 µM rac-[Rh(bpy)$_2$chrysi]$^{3+}$ on 1 µM 5'-[$^{32}$P] labeled 17mer duplex DNA of the sequence indicated containing a CC mismatch with the site of photocleavage by [Rh(bpy)$_2$chrysi]$^{3+}$. The right gel shows dimethyl sulfate (DMS) footprinting of duplex DNA containing a CC mismatch in which the Lanes (left to right) are: Maxam-Gilbert sequencing (C+T; A+G); (3) DMS alone; (4) oxaliplatin at 1 µM; (5) RhPt at 1 µM; (6) RhPt at 50 µM, in which bands of high electrophoretic mobility indicate cleavage at guanine residues; covalent binding of platinum to guanine inhibits cleavage.
Figure 20:
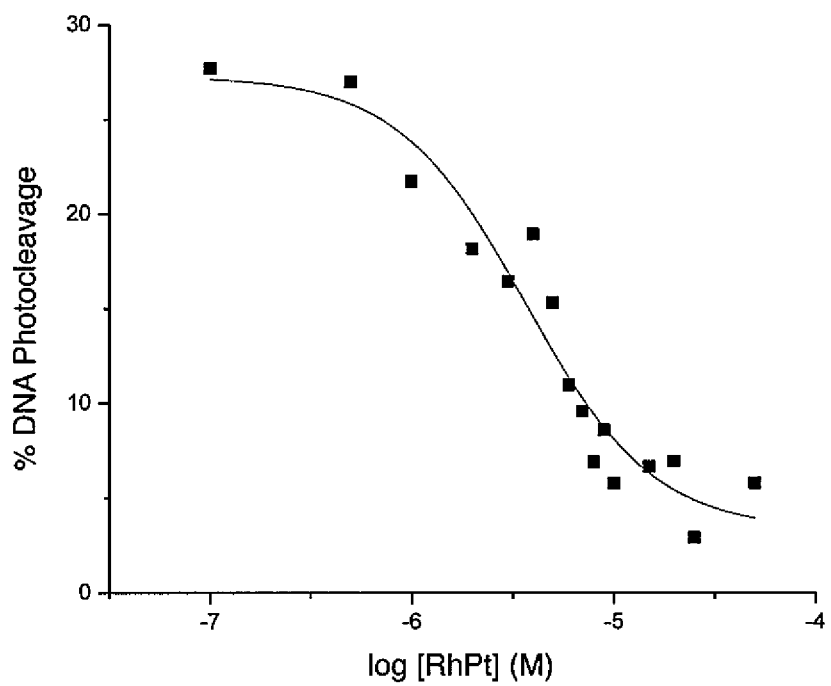
FIG. 20 is a representative sigmoidal curve showing the amount (%) of DNA cleavage of competition titrations between 1 µM [Rh(bpy)2chrysi]3+ and 0-50 µM of [Rh(chrysi)(HDPA)(Amal)Pt(DACH)]$^{3+}$ (RhPT) for binding constant determination at the CC mismatch, according to embodiments of the present invention.
Figure 21:
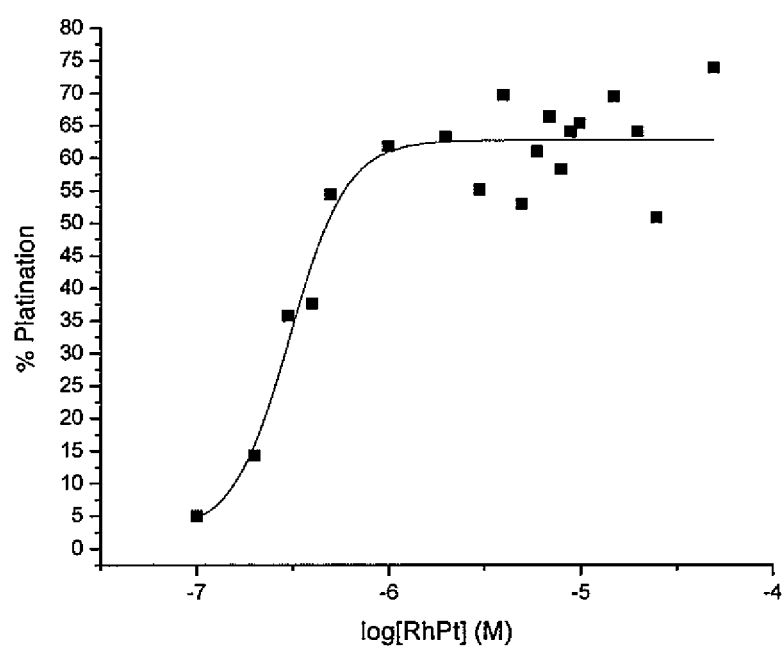
FIG. 21 is a representative sigmoidal curve fit of DNA platination (% platination) by the platinum subunit of [Rh(chrysi)(HDPA)(Amal)Pt(DACH)]$^{3+}$ (RhPT) from 0-50 µM, according to embodiments of the present invention.
Figure 22C:
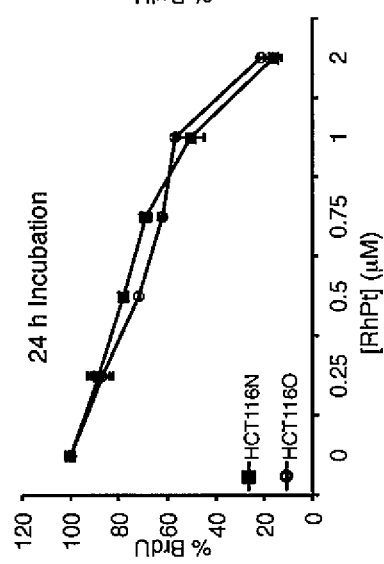
FIG. 22C is a graph of the amount (%) of BrdU incorporation as a function of [cisplatin] concentration (1-2 µM) in HCT116N (squares) and HCT116O (circles) cell lines after a 24 hour incubation, according to embodiments of the present invention.
Figure 22B:
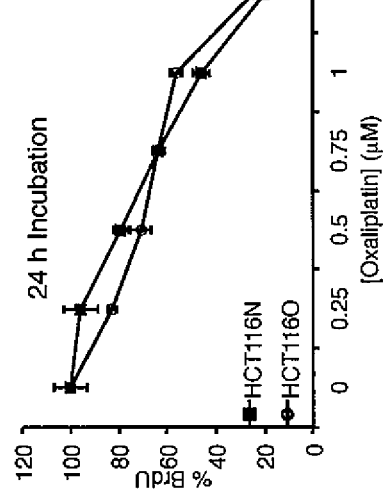
FIG. 22B is a graph of the amount (%) of BrdU incorporation as a function of [oxaliplatin] concentration (1-2 µM) in HCT116N (squares) and HCT116O (circles) cell lines after a 24 hour incubation, according to embodiments of the present invention.
Figure 22A:
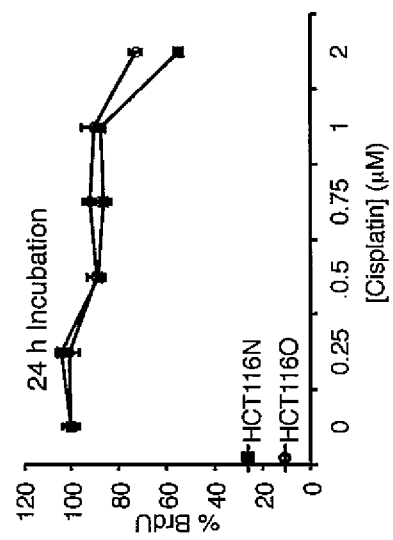
FIG. 22A is a graph of the amount (%) of BrdU incorporation as a function of [Rh(chrysi)(HDPA)(Amal)Pt(DACH)]$^{3+}$ (RhPT) concentration (1-2 µM) in HCT116N (squares) and HCT116O (circles) cell lines after a 24 hour incubation, according to embodiments of the present invention.
Figure 23:
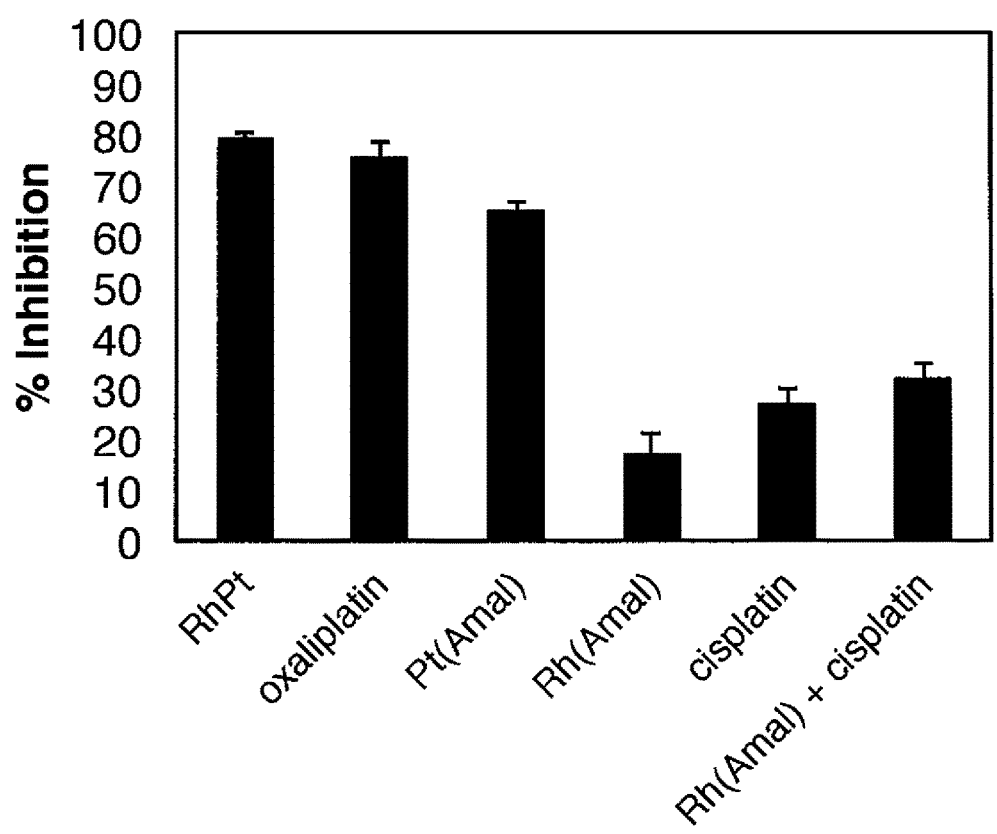
FIG. 23 is a graph of the amount (%) of growth inhibition of HCT116O cells, as measured by BrdU incorporation, after 24 hours of incubation with 2 µM of RhPt, oxaliplatin, Pt(Amal), cisplatin, or Rh(Amal) and cisplatin as indicated, according to embodiments of the present invention.
Figure 25:
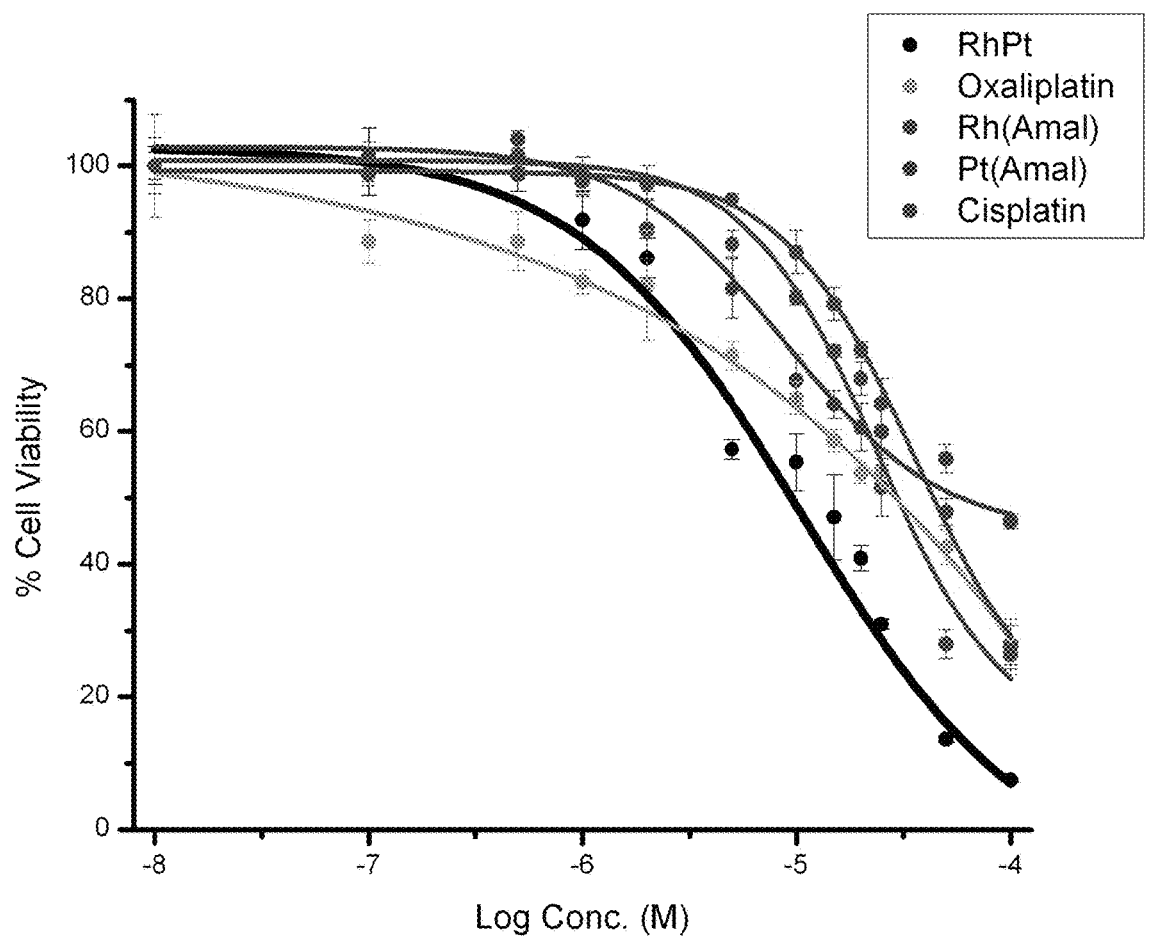
FIG. 25 is a graph depicting dose-response cytotoxicity curves of HCT116O cells treated with 0-100 µM of RhPt (black line), oxaliplatin (orange), Rh(Amal) (red), Pt(Amal) (purple), or cisplatin (green) for 72 hours and then treated with MTT reagent, according to embodiments of the present invention.

For [RhPt] Conjugate, a single-stranded DNA oligomer with the sequence 5'-TTAGGATCATCCATATA-3' (SEQ. ID NO: 2) (underline denotes the mismatch) was labeled at the 5'-end with [$^{32}$P]-ATP and polynucleotide kinase (PNK) at 37° C. for 1 h. The radiolabeled DNA was purified by gel electrophoresis and annealed to its mismatched complement (containing a CC mismatch) by heating to 90° C. in buffer (100 mM NaCl, 20 mM NaP$_i$, pH 7.1), followed by slow cooling to ambient temperature over 3 h, to give a final concentration of 2 µM duplex DNA. Racemic solutions of the metal complex (containing all stereoisomers) were prepared in Milli-Q water over a range of concentrations (100 nM-50 µM). For each sample, 4 µM rac-[Rh(bpy)$_2$chrysi]Cl$_3$ (5 µl), which photocleaves DNA at mismatched sites, 2 µM annealed mismatched duplex DNA (10 µl), and the non-photocleaving competitor complex at various concentrations (5 µl) were combined to give 1 µM rac-[Rh(bpy)$_2$chrysi]Cl$_3$ and 1 µM duplex DNA as the final concentrations. A "light" control, (ØRh, ØPt) consisting of 2 µM DNA mixed with 10 µl Milli-Q water, and a "dark" control (Øhυ), containing the DNA mixed with the highest concentration of competitor complex without irradiation, were also prepared. The samples were vortexed and, except for the dark control, irradiated on an Oriel (Darmstadt, Germany) 1000-W Hg/Xe solar simulator (340-440 nm) for 15 min. The samples were then incubated at 37° C. for 10 minutes to degrade any metastable products and dried under vacuum. The irradiated samples were electrophoresed on a 20% denaturing polyacrylamide gel and exposed to a phosphor screen (FIG. 17). The amounts of DNA in each band were analyzed by autoradiography and quantitated by phosphorimagery (ImageQuant) (FIG. 20).

Example 17. Binding Constant Determination as Disclosed in FIG. 12

To assess the binding of the rhodium subunit of [Rh(chrysi)(phen)(DPE-Pt(NH$_3$)$_2$Cl)]$^{3+}$ at the CC mismatch, the fraction of cleaved DNA in each lane on the gel was quantified and expressed as a percentage of the total DNA in each lane and plotted against the log of the concentration of [Rh(chrysi)(phen)(DPE-Pt(NH$_3$)$_2$Cl)]$^{3+}$. The data from three independent titration experiments were each fit to a sigmoidal curve using OriginPro 8.5. The concentration of rhodium at the inflection point at the curve ([Rh$_{50\%}$]) was then used to solve simultaneous equilibria involving DNA, [Rh(bpy)$_2$chrysi]Cl$_3$, and [Rh(chrysi)(phen)(DPE-Pt(NH$_3$)$_2$Cl)]$^{3+}$ in Mathematica 8.0 to obtain the binding constant (K$_B$).

Example 18. Binding Constant Determination as Disclosed in FIG. 20

As the RhPt complex does not photocleave DNA upon irradiation, the binding affinity for a CC mismatch was determined via a competition titration against rac-[Rh(bpy)2chrysi]3+, which does photocleave DNA at mismatched sites. To assess the binding of the rhodium subunit of RhPt at the CC mismatch, the fraction of cleaved DNA was quantified and expressed as a percentage of the total DNA in each lane and plotted against the log of the concentration of RhPt. The data from three independent titration experiments were each fit to a sigmoidal curve using OriginPro 8.5. The concentration of rhodium at the inflection point at the curve ([Rh50%]) was then used to solve simultaneous equilibria involving DNA, [Rh(bpy)2chrysi]Cl3, and RhPt in Mathematica 8.0 to obtain the binding constant (KB).

Example 19. Platinum Binding to Mismatched and Well-Matched DNA as Disclosed in FIGS. 7 and 13

Figure 13:
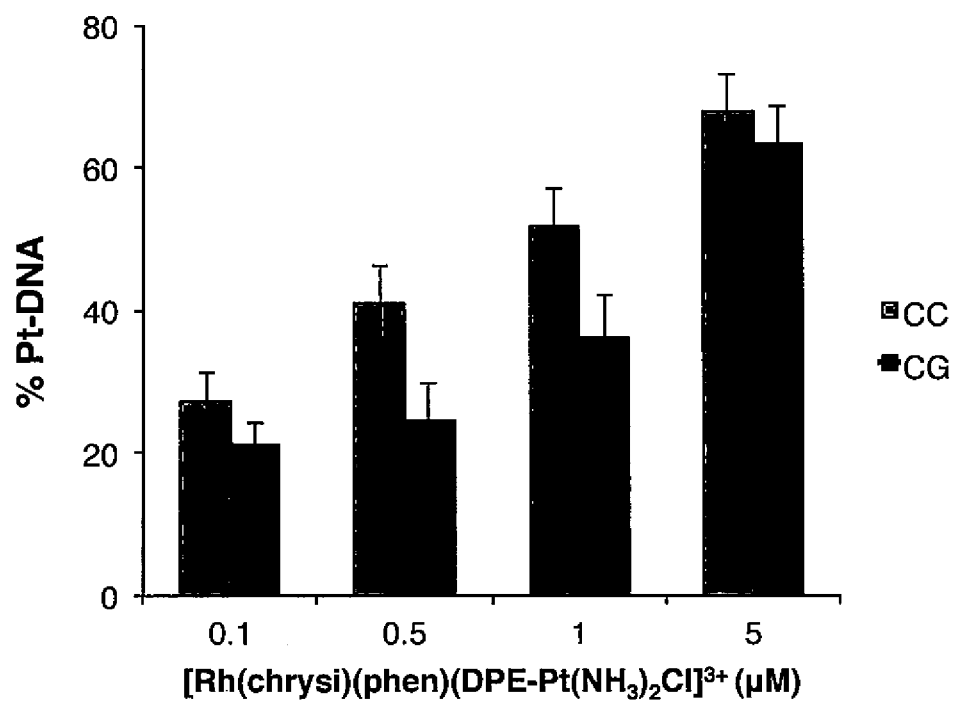
FIG. 13 is a graph showing the quantification of platination (% Pt-DNA) of mismatched CC (solid bars) and well-matched CG (lined bars) duplex DNA at 1 μM as a function of [Rh(chrysi)(phen)(DPE-Pt(NH$_3$)$_2$Cl]$^{3+}$ concentration of 0.1, 0.5, 1, and 5 µM as indicated, according to embodiments of the present invention.
Figure 15A:
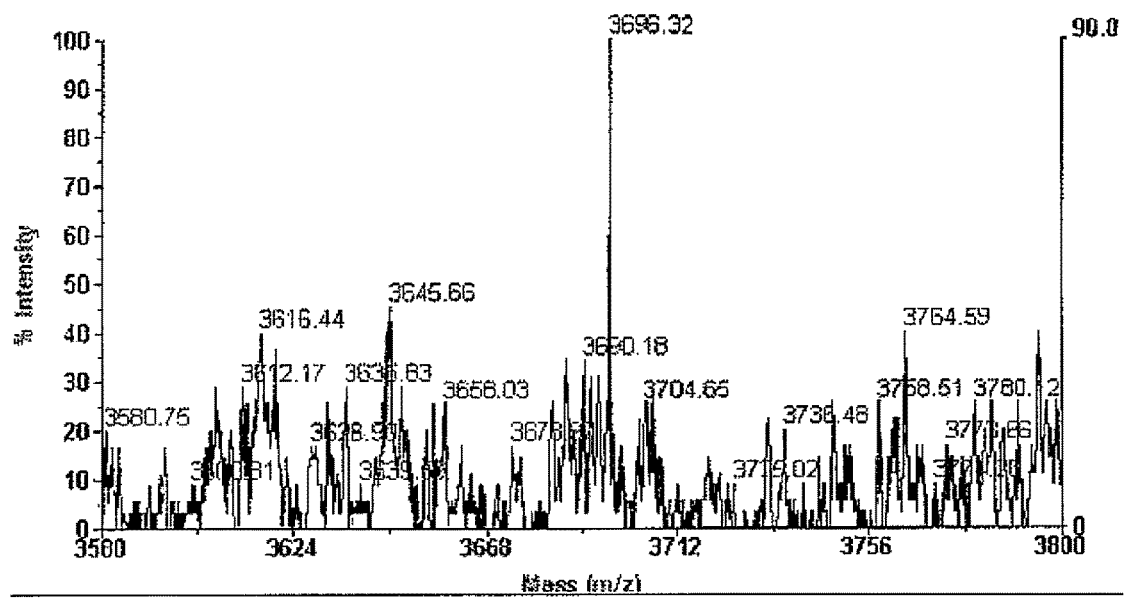
FIGS. 15A, 15B, 15C, 15D, and 15E are MALDI-TOF mass spectrometry spectra of platinated DNA fragments, according to embodiments of the present invention.
Figure 15B:
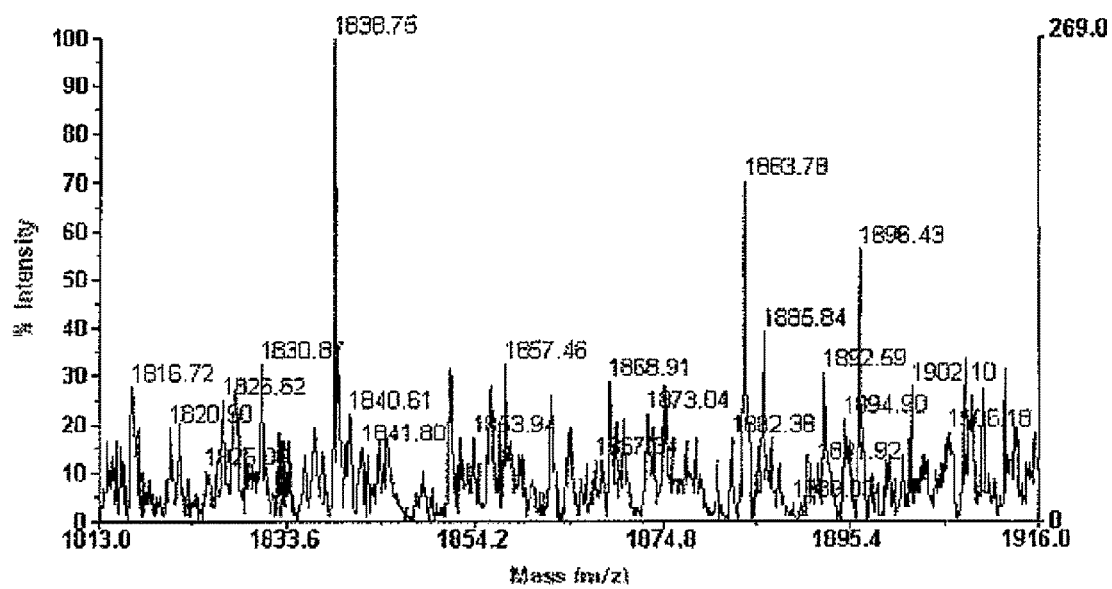
Figure 15C:
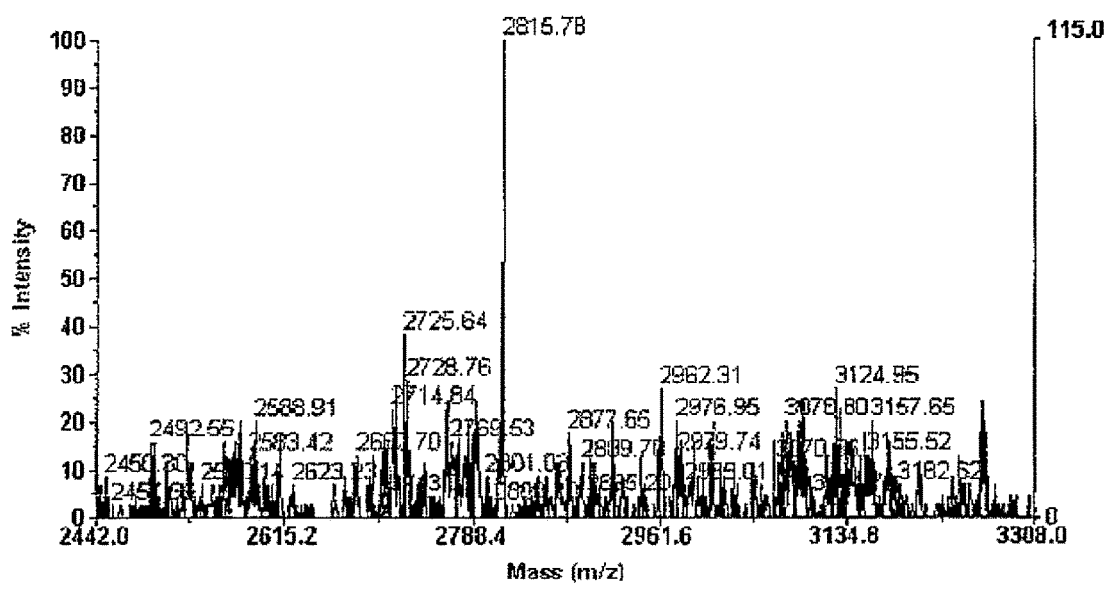
Figure 15D:
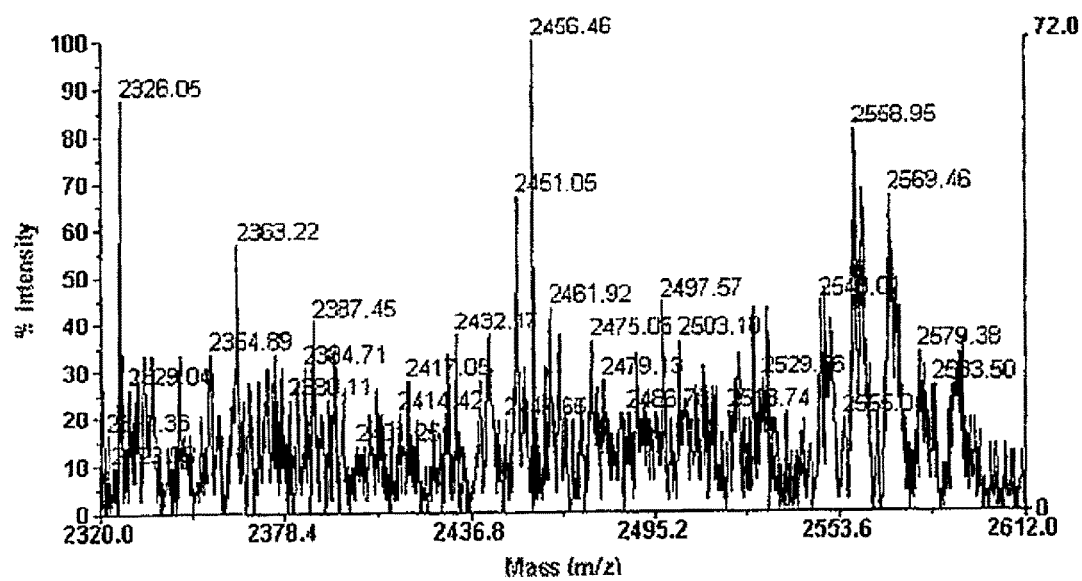
Figure 15E:
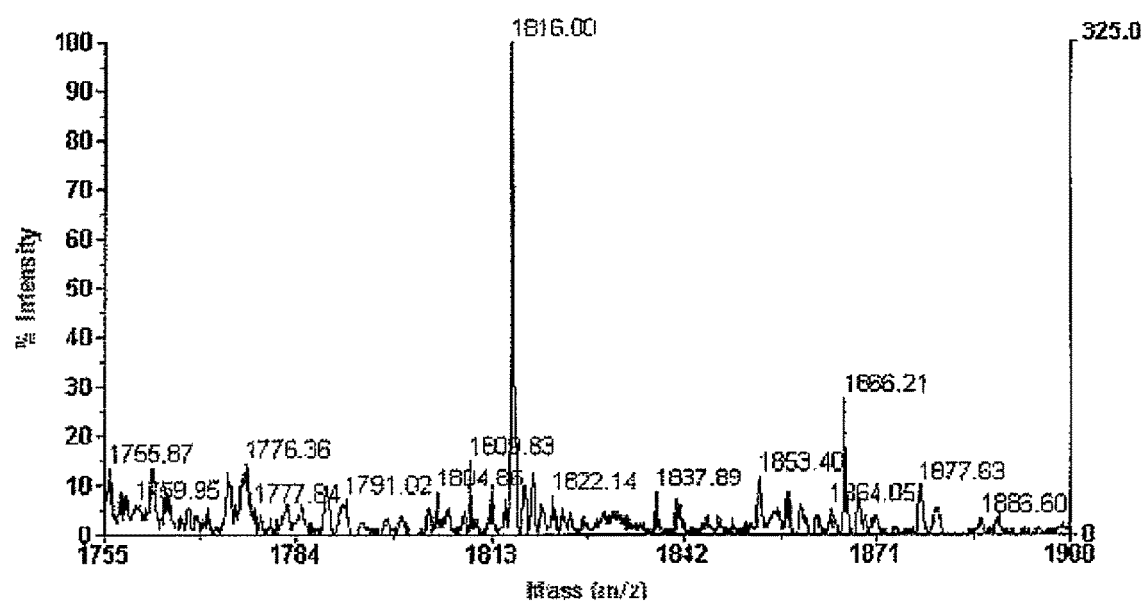
Figure 16:
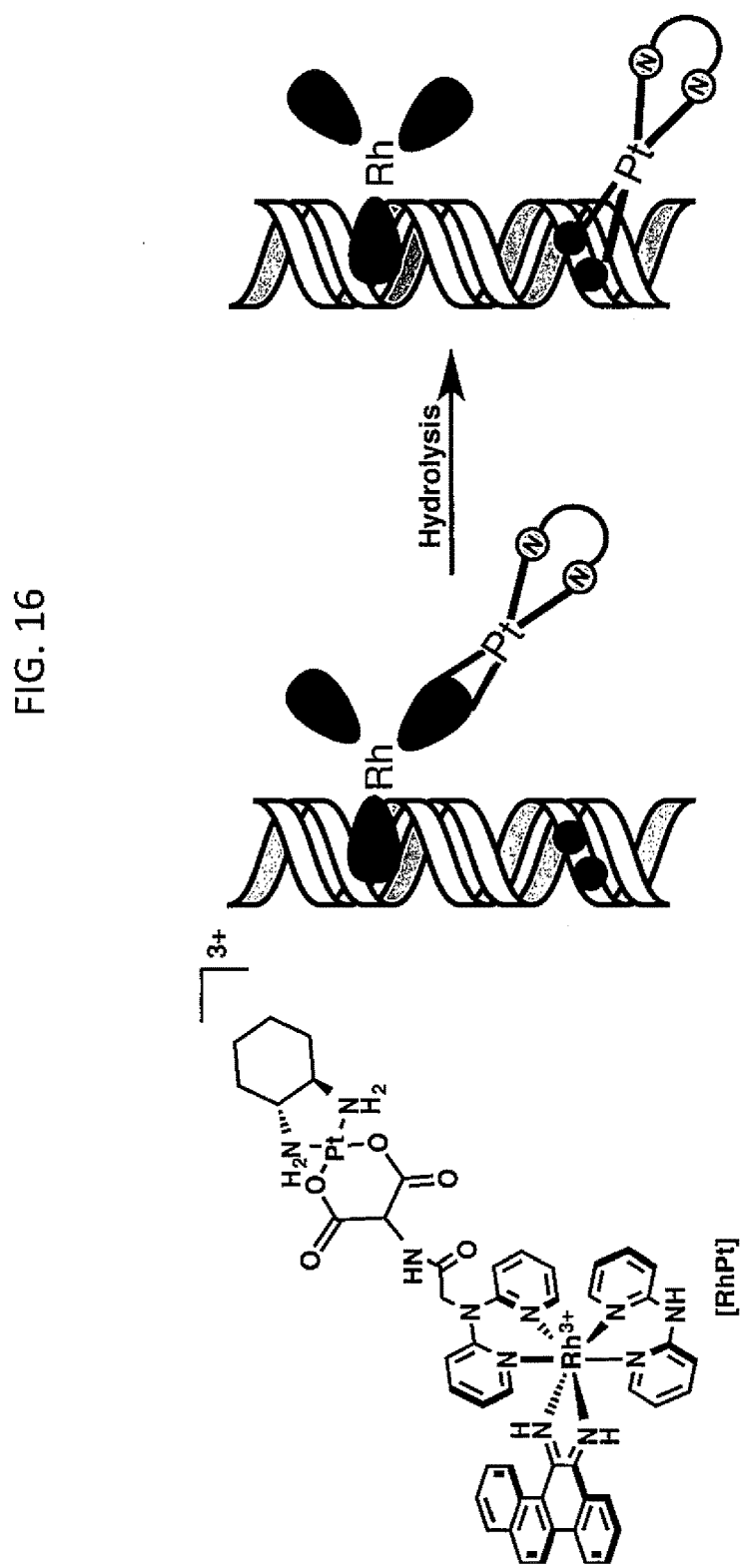
FIG. 16 is a schematic showing the bifunctionality of the [Rh(chrysi)(HDPA)(Amal)Pt(DACH)]$^{3+}$ conjugate (abbreviated as RhPt) with mismatched DNA, according to embodiments of the present invention.

A single-stranded DNA oligomer with the sequence 5*'-TTAGGATCATCCATATA-3'(SEQ ID NO: 2) (underline denotes the mismatch, asterisk denotes the radiolabel) was labeled at the 5'-end with [$^{32}$P]-ATP and polynucleotide kinase (PNK) at 37° C. for 2 h. The radiolabeled DNA was purified by gel electrophoresis and annealed to either its mismatched complement (containing a CC mismatch) or a fully matched complement strand by heating to 90° C. in buffer (100 mM NaCl, 20 mM NaP$_i$, pH 7.1), followed by slow cooling to ambient temperature over 2 h, to give a final concentration of 2 µM duplex DNA. Racemic solutions of [Rh(chrysi)(phen)(DPE-Pt(NH$_3$)$_2$Cl)]$^{3+}$ were prepared in 50 mM NaCl$_{(aq)}$ over a range of concentrations (100 nM-5 µM). For each sample, 2 µM annealed mismatched duplex DNA (10 µl) was mixed with [Rh(chrysi)(phen)(DPE-Pt(NH$_3$)$_2$Cl)]$^{3+}$ at various concentrations (10 µl) to give 1 µM duplex DNA and 75 mM NaCl$_{(aq)}$ as the final concentrations. A "light" control, (ØRh, ØPt) consisting of 2 µM DNA mixed with 10 µl Milli-Q water, and a "dark" control (Øhυ), containing the DNA mixed with the highest concentration of metalloinsertor without irradiation, were also prepared. The samples were incubated at 37° C. for periods of 1, 3, or 18 h to promote the formation of the platinated DNA adducts. After the incubation period, samples were quenched with 50 µl of 0.1 M NaCl$_{(aq)}$ and cooled to 4° C. for 30 min. Except for the unirradiated controls, samples were irradiated on an Oriel (Darmstadt, Germany) 1000-W Hg/Xe solar simulator (340-440 nm) for 15 min and dried in vacuo. For DNA footprinting experiments, platinated DNA was precipitated with ethanol and subject to the appropriate sequencing method. The irradiated samples were electrophoresed on a 20% denaturing polyacrylamide gel and exposed to a phosphor screen (FIG. 7). The amounts of DNA in each band were analyzed by autoradiography and quantitated by phosphorimagery (ImageQuant) (FIG. 13).

Example 20. Dimethyl Sulfate Footprinting of Platinated DNA as Disclosed in FIG. 8

Figure 8:
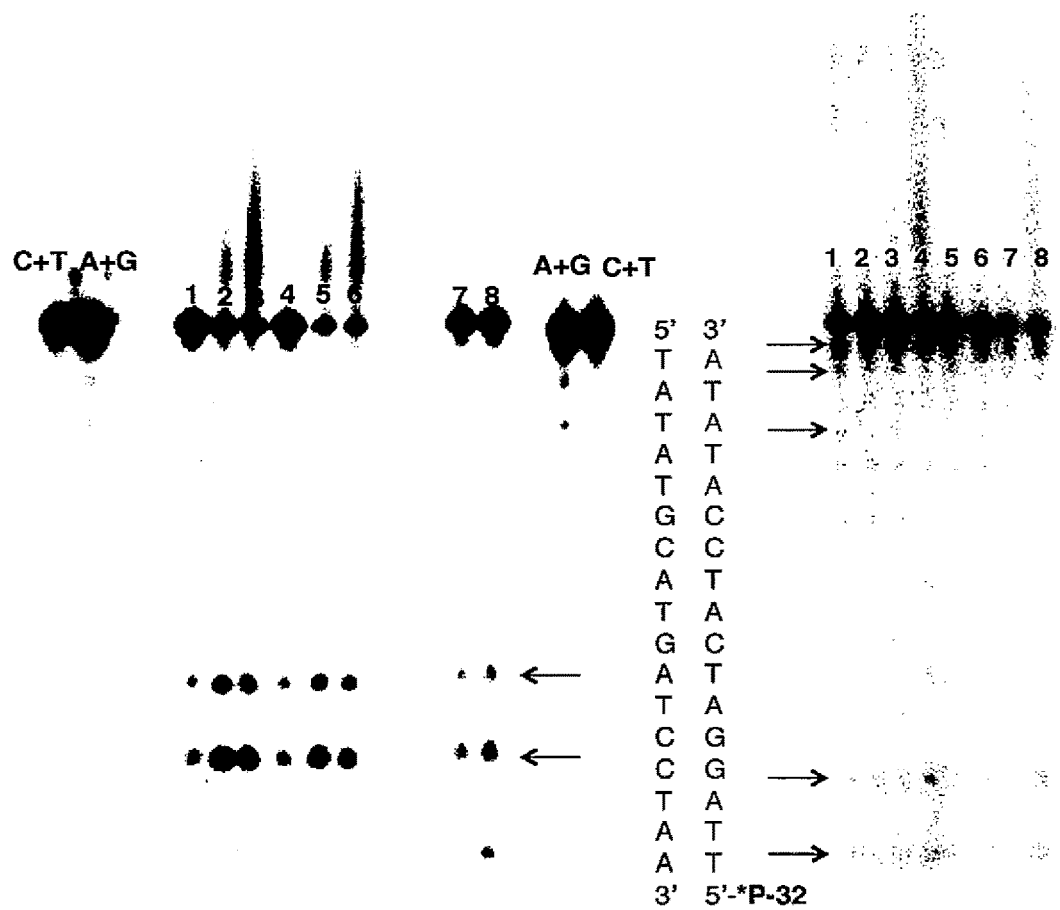
FIG. 8 shows DNA sequencing gels used to determine the site of platinum binding, according to embodiments of the present invention. The left gel shows dimethyl sulfate (DMS) footprinting of 5'-end radiolabeled duplex DNA containing a CC mismatch and a d(GpG) site with Lanes 1-8 as follows: (1) CC-mismatched DNA in the absence of platinum; (2) mismatched DNA with 1 μM conjugate; (3) mismatched DNA with 5 μM conjugate; (4) well-matched DNA in the absence of platinum; (5) well-matched DNA with 1 μM conjugate; (6) well-matched DNA with 5 μM conjugate; (7) mismatched DNA with 1 μM cisplatin; (8) well-matched DNA with 1 μM cisplatin; Maxam-Gilbert sequencing lanes (C+T; A+G) are indicated. The right gel shows methylmethanemonosulfate (MMS) footprinting of adenine residues in the same sequence as in the left gel, in which samples were incubated with platinum, treated with 5 mM MMS for 18 hours, and depurinated by neutral thermal hydrolysis followed by piperidine cleavage, with Lanes 1-8 as follows: (1) CC-mismatched DNA in the absence of platinum; (2) mismatched DNA with 1 μM cisplatin; (3) mismatched DNA with 1 μM conjugate; (4) mismatched DNA with 5 μM conjugate; (5) well-matched DNA in the absence of platinum; (6) well-matched DNA with 1 μM cisplatin; (7) well-matched DNA with 1 μM conjugate; (8) well-matched DNA with 5 μM conjugate.
Figure 10A:
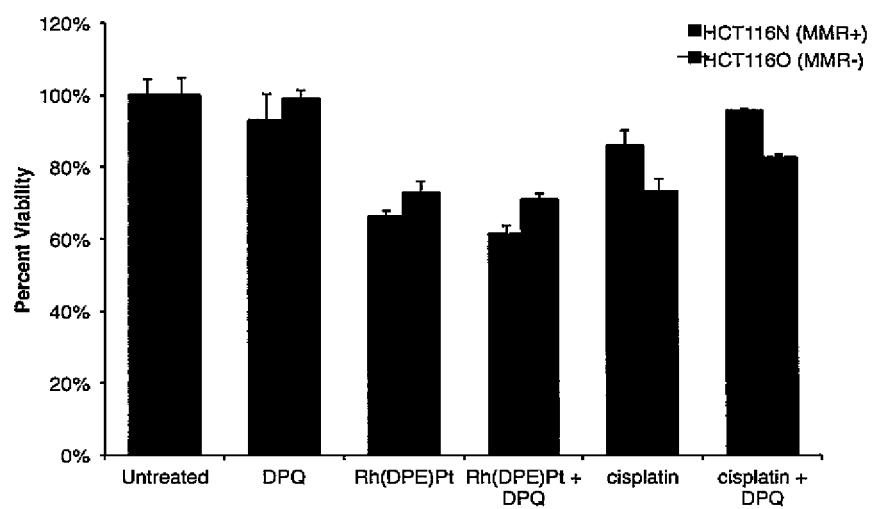
FIG. 10A is a graph comparing the percent (%) viability of HCT116N (solid bars) and HCT116O (lined bars) cells untreated (control) or treated with the PARP inhibitor DPQ at 50 μM, [Rh(chrysi)(phen)(DPE-Pt(NH$_3$)$_2$Cl)]$^{3+}$ (Rh(DPE) Pt) at 5 μM, cisplatin at 5 μM, or combinations of Rh(DPE) Pt or cisplatin with DPQ, as indicated, according to embodiments of the present invention.
Figure 10B:
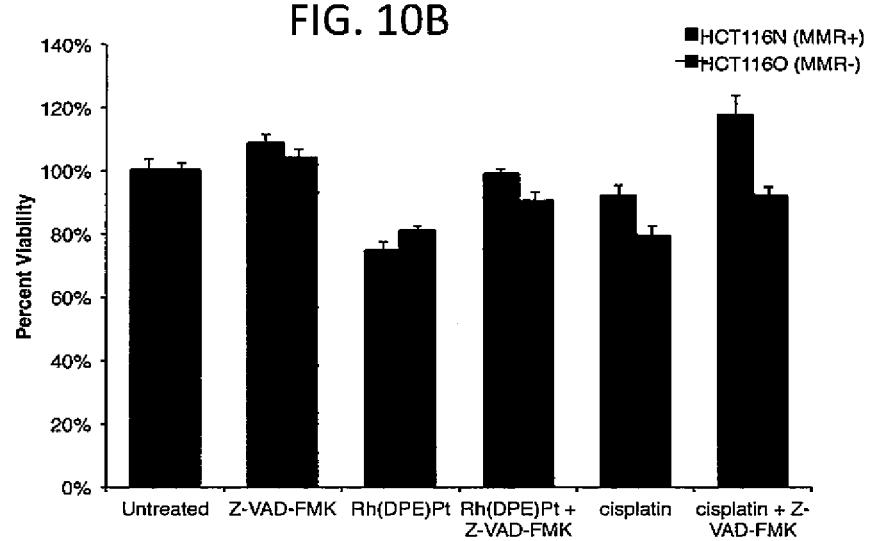
FIG. 10B is as graph comparing the percent (5) viability of HCT116N (solid bars) and HCT116O (lined bars) cells untreated (control) or treated with the caspase inhibitor Z-VAD-FMK at 35 μM), [Rh(chrysi)(phen)(DPE-Pt(NH$_3$)$_2$Cl)]$^{3+}$ (Rh(DPE)Pt) at 5 μM, cisplatin at 5 μM, or combinations of Rh(DPE)Pt or cisplatin with Z-VAD-FMK, as indicated, according to embodiments of the present invention.
Figure 11:
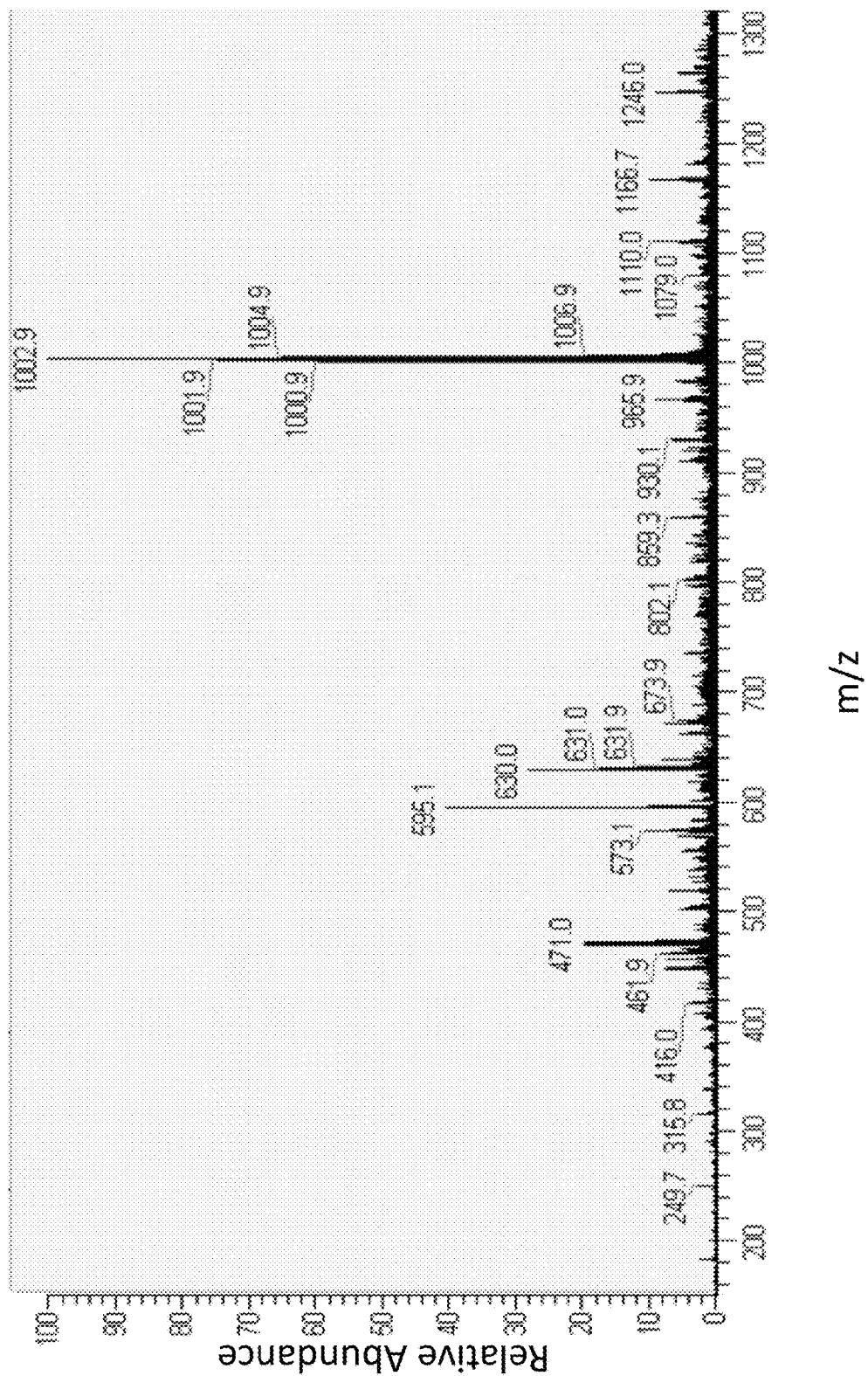
FIG. 11 is an electrospray ionization mass spectrometry (ESI-MS) spectrum of [Rh(chrysi)(phen)(DPE-Pt(NH$_3$)$_2$Cl)]$^{3+}$ with m/z=1000.9-1006.9 indicative of the Rh and Pt isotope patterns, according to embodiments of the present invention.

DNA footprinting of guanine by dimethyl sulfate (DMS) was carried out according to literature procedures, as disclosed in Brabec et al., *PNAS*, 1993, 90, 5345-5349, the entire contents of which are herein incorporated by reference. Radiolabeled duplex DNA (well-matched or CC-mismatched; see above for sequence) was platinated with varying concentrations of [Rh(chrysi)(phen)(DPE-Pt(NH$_3$)$_2$Cl)]$^{3+}$ (0, 1, or 5 µM) or cisplatin (1 µM) as described above. The platination reaction was quenched via addition of 0.1 M NaCl$_{(aq)}$ (0.1 ml) followed by cooling to 4° C. for 30 min. Samples were purified by ethanol precipitation and dried in vacuo. The samples were taken up in 5 µl Milli-Q water, diluted with DMS buffer (50 mM sodium cacodylate, 1 mM EDTA, pH 7.5) (190 µl), and 2 mM calf-thymus DNA (4 µl) was added as a carrier DNA. Samples were cooled to 0° C. and treated with 5 µl DMS (10% v/v in EtOH, prepared immediately before use) for 5 min at 25° C. The reaction was quenched via addition of the DMS stop solution (1.5 M NaOAc, 1 M β-mercaptoethanol, 250 µg/ml yeast tRNA) at 0° C. Following ethanol precipitation of the DNA, samples were treated with 10% aqueous piperidine and heated to 90° C. for 30 min. The piperidine was removed in vacuo, and samples were electrophoresed on a 20% denaturing polyacrylamide gel and exposed to a phosphor screen (FIG. 8). The amounts of DNA in each band were analyzed by autoradiography and quantitated by phosphorimagery (ImageQuant).

Example 21. Methylation of Platinated DNA with Methyl Methanesulfonate (MMS), as Disclosed in FIGS. 8 and 14

Radiolabeled duplex DNA (well-matched or CC-mismatched; see above for sequence) was platinated with varying concentrations of [Rh(chrysi)(phen)(DPE-Pt(NH$_3$)$_2$Cl)]$^{3+}$ (0, 1, or 5 μM) or cisplatin (1 μM) as described above for DMS. The platination reaction was quenched via addition of 0.1 M NaCl$_{(aq)}$ (0.1 ml) followed by cooling to 4° C. for 30 min. Samples were purified by ethanol precipitation and dried in vacuo. The samples were taken up in 10 μl Milli-Q water, diluted with Tris-HCl buffer (10 mM Tris-HCl, 5 mM MMS, pH 7.8) (200 μl), and 2 mM calf-thymus DNA (4 μl) was added as a carrier DNA. The DNA methylation reaction was allowed to occur at ambient temperature for 16 h, followed by ethanol precipitation. Strand breaks in the reacted DNA were generated by heating methylated DNA in 10 mM Tris-HCl buffer (0.1 ml) at 90° C. for 15 min to depurinate thermally labile adducts. Following precipitation with ethanol, DNA was then treated with 1 M piperidine at 90° C. for 30 min. Samples were then dried in vacuo, electrophoresed on a 20% denaturing polyacrylamide gel, and exposed to a phosphor screen (FIG. 8). The amounts of DNA in each band were analyzed by autoradiography and quantitated by phosphorimagery (ImageQuant) (FIG. 14).

Example 22. Analysis of Platinated DNA by Mass Spectrometry, as Disclosed in FIGS. 15A-15E

Duplex DNA (1 μM well-matched or CC-mismatched; see above for sequence) was platinated with 5 μM [Rh(chrysi)(phen)(DPE-Pt(NH$_3$)$_2$Cl)]$^{3+}$ and incubated alongside unplatinated duplex DNA at 37° C. for 90 min. The reaction was quenched via incubation at 4° C. for 15 min, and the samples were irradiated for 15 min. The DNA was then treated with 1 M piperidine formate at 60° C. for 15 min, precipitated with ethanol at 4° C., and depurinated with 1 M piperidine at 90° C. for 15 min. The piperidine was removed in vacuo and the dried DNA samples were analyzed by MALDI-TOF mass spectrometry.

As disclosed throughout and evidenced by the selective cytotoxicity data of FIGS. 5, 9A, 10, and 19, metalloinsertor conjugates of the present invention provide a means for selectively targeting MMR-deficient cells, as well as improving platinum anticancer compounds.

While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:

1. A composition comprising a complex selected from the group consisting of [M$^{m+}$(chrysi)(phen)(HPBA)], [M$^{m+}$(phen)(chrysi)(DPE-Pt(NH$_3$)$_2$Cl)], [M$^{m+}$(chrysi)(HDPA)(Amal)(Pt)(DACH)], and [M$^{m+}$(chrysi)(phen)(L-Cysteine)], wherein:
M is rhodium;
m is 2 or 3;
chrysi is chrysene-5,6-diimine;

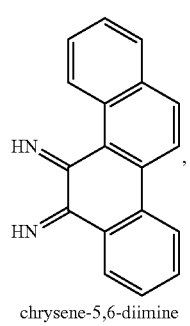 [SMILES: N=C1C(=N)c2c(ccc3ccccc23)-c2ccccc21]

chrysene-5,6-diimine phen is:

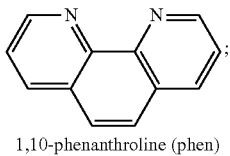 [SMILES: c1cnc2c(c1)ccc1cccnc12]

1,10-phenanthroline (phen)

DPE is:

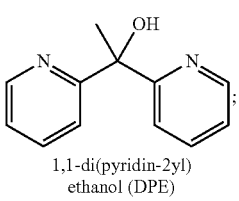

1,1-di(pyridin-2yl) ethanol (DPE)

HDPA is:

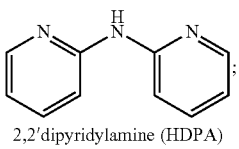 [SMILES: c1ccc(Nc2ccccn2)nc1]

2,2′dipyridylamine (HDPA)

$[DPE-Pt(NH_3)^2Cl]^{1+}$ is:

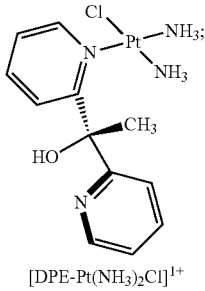

$[DPE-Pt(NH_3)_2Cl]^{1+}$

L-cysteine is:

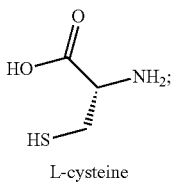

L-cysteine

HPBA is:

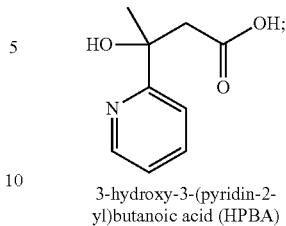

3-hydroxy-3-(pyridin-2-yl)butanoic acid (HPBA)

and

[(Amal)(Pt)(DACH)] is:

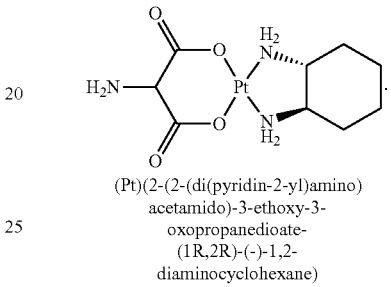

(Pt)(2-(2-(di(pyridin-2-yl)amino) acetamido)-3-ethoxy-3-oxopropanedioate-(1R,2R)-(-)-1,2-diaminocyclohexane)

2. A composition comprising a complex represented by $[Rh(phen)(chrysi)(DPE-Pt(NH_3)_2Cl)]^{3+}$
wherein:
phen is:

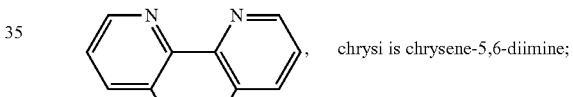, chrysi is chrysene-5,6-diimine;

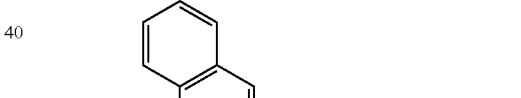, and $[DPE-Pt(NH_3)_2Cl]^+$ is:

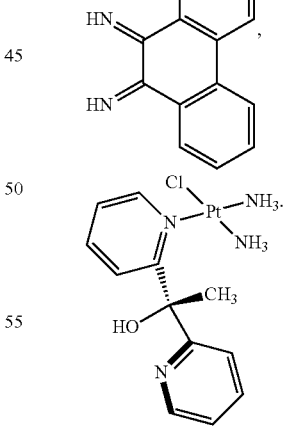

3. The composition of claim 1, wherein the complex is selected from the group consisting of $[Rh(chrysi)(phen)(HPBA)]^{2+}$, $[Rh(chrysi)(phen)(L-cysteine)]^{2+}$, $[Rh(chrysi)(phen)(DPE-Pt(NH_3)_2Cl)]^{3+}$, and $[Rh(chrysi)(HDPA)(Amal)(Pt)(DACH)]^{3+}$.

4. A method of selectively inducing cytotoxicity in mismatch repair (MMR)-deficient cells, comprising:

providing the composition of claim 2 to the MMR-deficient cells.

5. The method of claim 4, comprises providing the composition in vitro.

6. The method of claim 4, comprises providing the composition in vivo.

7. A method of selectively decreasing cell proliferation, comprising:

providing the composition of claim 2 to MMR-deficient cells.

8. The method of claim 7, comprises providing the composition in vitro.

9. The method of claim 7, comprises providing the composition in vivo.

10. A pharmaceutical composition, comprising:

an effective amount of the composition of claim 1; and a pharmaceutically acceptable carrier.

* * * * *